US008470770B2

(12) United States Patent  
Mor et al.

(10) Patent No.: US 8,470,770 B2
(45) Date of Patent: *Jun. 25, 2013

(54) ANTIMICROBIAL AGENTS

(75) Inventors: Amram Mor, Nesher (IL); Inna Radzishevsky, Beer-Sheva (IL)

(73) Assignee: Technion Research & Development Foundation Ltd., Haifa (IL)

(*) Notice: Subject to any disclaimer, the term of this patent is extended or adjusted under 35 U.S.C. 154(b) by 503 days.

This patent is subject to a terminal disclaimer.

(21) Appl. No.: 12/598,057

(22) PCT Filed: Apr. 28, 2008

(86) PCT No.: PCT/IL2008/000563
§ 371 (c)(1),
(2), (4) Date: Oct. 29, 2009

(87) PCT Pub. No.: WO2008/132737
PCT Pub. Date: Nov. 6, 2008

(65) Prior Publication Data
US 2010/0120671 A1 May 13, 2010

Related U.S. Application Data

(60) Provisional application No. 60/924,087, filed on Apr. 30, 2007.

(51) Int. Cl.
*A61K 38/12* (2006.01)
(52) U.S. Cl.
USPC .......................................... 514/2.3; 514/21.1
(58) Field of Classification Search
None
See application file for complete search history.

(56) References Cited

U.S. PATENT DOCUMENTS

| | | | |
|---|---|---|---|
| 5,965,525 | A | 10/1999 | Burkhardt et al. |
| 5,972,379 | A | 10/1999 | Guo et al. |
| 6,127,337 | A | 10/2000 | Konishi |
| 6,548,048 | B1 | 4/2003 | Cuthbertson et al. |
| 6,566,324 | B2 | 5/2003 | Nadel et al. |
| 6,571,790 | B1 | 6/2003 | Weinstein |
| 6,637,430 | B1 | 10/2003 | Voges et al. |
| 6,652,323 | B2 | 11/2003 | Yanda |
| 6,656,969 | B2 | 12/2003 | Young |
| 7,504,381 | B2 | 3/2009 | Mor et al. |
| 2003/0036628 | A1 | 2/2003 | Zheleva et al. |
| 2003/0083237 | A1 | 5/2003 | Dou et al. |
| 2003/0171539 | A1 | 9/2003 | Quentin et al. |
| 2004/0110228 | A1* | 6/2004 | McAlpine et al. ............. 435/7.1 |
| 2005/0118678 | A1 | 6/2005 | Mayo |
| 2006/0074021 | A1 | 4/2006 | Mor et al. |
| 2007/0032428 | A1 | 2/2007 | Mor et al. |
| 2010/0278807 | A1 | 11/2010 | Mor et al. |
| 2012/0295837 | A1 | 11/2012 | Mor et al. |

FOREIGN PATENT DOCUMENTS

| | | |
|---|---|---|
| JP | 11-506326 | 6/1999 |
| JP | 2004-175727 | 6/2007 |
| WO | WO 96/38473 | 12/1996 |
| WO | WO 98/18501 | 5/1998 |
| WO | WO 98/25953 | 6/1998 |
| WO | WO 99/25381 | 5/1999 |
| WO | WO 00/76550 | 12/2000 |
| WO | WO 01/00676 | 1/2001 |
| WO | WO 03/035677 | 5/2003 |
| WO | WO 03/048201 | 6/2003 |
| WO | WO 2006/035431 | 4/2006 |
| WO | WO 2008/132737 | 11/2008 |
| WO | WO 2008/132738 | 11/2008 |

OTHER PUBLICATIONS

Zhang et al. ("Large Cyclic Peptides as Cores of Multivalent Ligands: Application to Inhibitors of Receptor Binding by Cholera Toxin," J. Org. Chem. 2004, 69, 7737-7740).*
Davies ("The Cyclization of Peptides and Depsipeptides," IJ. Peptide Sci., 2003, 9, 471-501).*
Dathe et al ("Cyclization Increases the Antimicrobial Activity and Selectivity of Arginine- and Tryptophan-Containing Hexapeptides," Biochemistry 2004, 43, 9140-9150).*
Tang et al. ("A cyclic Antimicrobial Peptide Produced in Primate Leukocytes by the Ligation of Two Truncated a-Defensins," Science, 1999, 286, 498-502).*
Oren et al. ("Cyclization of a Cytolytic Amphipathic α-Helical Peptide and Its Diastereomer: Effect on Structure, Interaction with Model Membranes, and Biological Function," Biochemistry, 2000, 39, 20, 6103-6114).*
Official Action Dated Sep. 8, 2010 From the US Patent and Trademark Office Re.: U.S. Appl. No. 12/232,383.
Communication Pursuant to Article 94(3) EPC Dated Sep. 21, 2011 From the European Patent Office Re. Application No. 08738265.1.
Acar "Consequences of Bacterial Resistance to Antibiotics in Medical Practice", Clinical Infectious Diseases, 24(Suppl.1): S17-S18, 1997.
Chapple et al. "Structure-Function Relationship of Antibacterial Synthetic Peptides Homologous to a Helical Surface Region on Human Lactoferrin Against *Escherichia coli* Serotype O111", Infection and Immunity, 66(6): 2434-2440, 1998.
Coote et al. "Inhibitory Action of a Truncated Derivative of the Amphibian Skin Peptide Dermaseptin S3 on *Saccharomyces cerevisiae*", Antimicrobial Agents and Chemotherapy, 42(9): 2160-2170, 1998.
Dagan et al. "In Vitro Antiplasmodium Effects of Dermaseptin S4 Derivatives", Antimicrobial Agents and Chemotherapy, 46(4): 1059-1066, 2002.
Feder et al. "Structure-Activity Relationship Study of Antimicrobial Dermaseptin S4 Showing the Consequences of Peptide Oligomerization on Selective Cytotoxicity", The Journal of Biological Chemistry, 275(6): 4230-4238, 2000. p. 4232, Table 1, p. 4234, 2nd Col.
Hancock et al. "Role of Membranes in the Activities of Antimicrobial Cationic Peptides", FEMS Microbiology Letters, 206: 143-149, 2002.

(Continued)

*Primary Examiner* — Christina Bradley

(57) ABSTRACT

New antimicrobial polymeric agents which are designed to exert antimicrobial activity while being stable, non-toxic and avoiding development of resistance thereto and a process of preparing same are disclosed. Further disclosed are pharmaceutical compositions containing same and a method of treating medical conditions associated with pathological microorganisms, a medical device, an imaging probe and a food preservative utilizing same.

16 Claims, No Drawings

OTHER PUBLICATIONS

Krugliak et al. "Antimalarial Activities of Dermaseptin S4 Derivatives", Antimicrobial Agents and Chemotherapy, 44(9): 2442-2451, 2000.
Kustanovich et al. "Structural Requirements for Potent Versus Selective Cytotoxicity for Antimicrobial Dermaseptin S4 Derivatives", The Journal of Biological Chemistry, 277(19): 16941-16951, 2002.
Loury et al. "Effect of Local Application of the Antimicrobial Peptide IB-367 on the Incidence and Severity of Oral Mucositis in Hamsters", Oral Surgery Oral Medicine Oral Pathology Oral Radiology Endod., 87(5): 544-551, 1999.
Mueller et al. "Antimicrobial Peptides as Potential New Antifungals", Mycoses, 42(Supp1.2): 77-82, 1999.
Examination Report Dated Sep. 24, 2010 From the Instituto Mexicano de la Propriedad Industrial Re. Application No. MX/a/2007/003608 and Its Summary Into English.
Translation of Decision on Rejection Dated Aug. 31, 2011 From the State Intellectual Property Office of the People's Republic of China Re.: Application No. 200580040186.2.
Translation of Office Action Dated Jan. 4, 2011 From the State Intellectual Property Office of the People's Republic of China Re.: Application No. 200580040186.2.
Communication Pursuant to Article 94(3) EPC Dated Jan. 24, 2008 From the European Patent Office Re.: Application No. 05788580.8.
Communication Relating to the Results of the Partial International Search Dated Feb. 4, 2009 From the International Searching Authority Re.: Application No. PCT/IL2008/000564.
Communication Relating to the Results of the Partial International Search Dated Nov. 30, 2006 From the International Searching Authority Re.: Application No. PCT/IL2005/001030.
International Preliminary Report on Patentability May 3, 2007 From the International Bureau of WIPO Re.: Application No. PCT/IL2005/001030.
Official Action Dated Jun. 6, 2008 From the US Patent and Trademark Office Re.: U.S. Appl. No. 11/234,183.
Official Action Dated Oct. 16, 2007 From the US Patent and Trademark Office Re.: U.S. Appl. No. 11/234,183.
International Preliminary Report on Patentability Dated Nov. 12, 2009 From the International Bureau of WIPO Re.: Application No. PCT/IL2008/000563.
International Preliminary Report on Patentability Dated Jul. 29, 2009 From the International Prelimiary Examining Authority Re.: Application No. PCT/IL2008/000564.
International Search Report Dated Apr. 1, 2009 From the International Searching Authority Re.: Application No. PCT/IL2008/000564.
International Search Report Dated Oct. 2, 2008 From the International Searching Authority Re.: Application No. PCT/IL2008/000563.
International Search Report Dated Feb. 28, 2007 From the International Searching Authority Re.: Application No. PCT/IL2005/001030.
Official Action Dated Sep. 4, 2009 From the US Patent and Trademark Office Re.: U.S. Appl. No. 11/500,461.
Official Action Dated Aug. 7, 2007 From the US Patent and Trademark Office Re.: U.S. Appl. No. 11/234,183.
Official Action Dated Sep. 8, 2008 From the US Patent and Trademark Office Re.: U.S. Appl. No. 11/500,461.
Official Action Dated Jan. 23, 2009 From the US Patent and Trademark Office Re.: U.S. Appl. No. 11/500,461.
Partial International Search Report Dated Nov. 30, 2006 From International Searching Authority Re.: Application No. PCT/IL2005/001030.
Translation of Office Action Dated Aug. 21, 2009 From the State Intellectual Property Office of the People's Republic of China Re.: Application No. 200580040186.2.
Written Opinion Dated Apr. 1, 2009 From the International Searching Authority Re.: Application No. PCT/IL2008/000564.
Written Opinion Dated Oct. 2, 2008 From the International Searching Authority Re.: Application No. PCT/IL2008/000563.
Written Opinion Dated Feb. 28, 2007 From the International Searching Authority Re.: Application No. PCT/IL2005/001030.
Aarbiou et al. "Human Neutrophil Defensins Induce Lung Epithelial Cell Proliferation In Vitro", Journal of Leukocyte Biology, 72: 167-174, 2002.
Alan et al. "Expression of a Magainin-Type Antimicrobial Peptide Gene (MSI-99) in Tomato Enhances Resistance to Bacterial Speck Disease", Plant Cell Reports, 22: 388-396, 2004.
Ammar et al. "Dermaseptin, A Peptide Antibiotic, Stimulates Microbicidal Activities of Polymorphonuclear Leukocytes", Biochemical and Biophysical Research Communications, 247: 870-875, 1998.
Andreu et al. "Animal Antimicrobial Peptides: An Overview", Biopolymers, 47: 415-433, 1998.
Appendini et al. "Antimicrobial Activity of a 14-Residue Synthetic Peptide Against Foodborne Microorganisms", Journal of Food Protection, 63(7): 889-893, 2000.
Avrahami et al. "Conjugation of a Magainin Analogue With Lipophilic Acids Controls Hydrophobicity, Solution Assembly, and Cell Selectivity", Biochemistry, 41: 2254-2263, 2002.
Avrahami et al. "Effect of Multiple Aliphatic Amino Acids Substitutions on the Structure, Function, and Mode of Action of Diastereomeric Membrane Active Peptides", Biochemistry, 40: 12591-12603, 2001.
Baker et al. "Anticancer Efficacy of Magainin2 and Analogue Peptides", Cancer Research, 53: 3052-3057, 1993.
Balaban et al. "A Chimeric Peptide Composed of a Dermaseptin Derivative and an RNA III-Inhibiting Peptide Prevents Graft-Associated Infections by Antibiotic-Resistant *Staphylococci*", Antimicrobial Agents and Chemotherapy, 48(7): 2544-2550, 2004.
Bassarello et al. "Tolaasins A-E, Five New Lipodepsipeptides Produced by *Pseudomonas tolaasii*", Journal of Natural Products, 67: 811-816, 2004.
Belaid et al. "In Vitro Antiviral Activity of Dermaseptins Against Herpes Simplex Virus Type 1", Journal of Medical Virology, 66: 229-234, 2002.
Blazyk et al. "A Novel Linear Amphipathic Beta-Sheet Cationic Antimicrobial Peptide With Enhanced Selectivity for Bacterial Lipids", The Journal of Biological Chemistry, 276(30): 27899-27906, 2001.
Blondelle et al. "Combinatorial Libraries: A Tool to Design Antimicrobial and Antifungal Peptide Analogues Having Lytic Specificities for Structure-Activity Relationship Studies", Biopolymers, 55: 74-87, 2000.
Boman "Antibacterial Peptides: Basic Facts and Emerging Concepts", Journal of Internal Medicine, 254: 197-215, 2003.
Brand et al. "Dermaseptins From *Phyllomedusa oreades* and *Phyllomedusa distincta*. Anti-Tryponasoma Cruzi Activity Without Cytotoxicity to Mammalian Cells", The Journal of Biological Chemistry, 277(51): 49332-49340, 2002.
Brogden et al. "Anitmicrobial Peptides in Animals and Their Role in Host Defences", International Journal of Antimicrobial Agents, 22: 465-478, 2003.
Brul et al. "Preservative Agents in Foods. Mode of Action and Microbial Resistance Mechanisms", International Journal of Food Microbiology, 50: 1-17, 1999.
CAS "Protein Sequences in the CAS Registry File on STN—Exact and Pattern Searching. A Quick Reference Guide", CAS Customer Care, American Chemical Society, XP007906932, p. 11, 2004.
Charpentier et al. "Structure, Synthesis, and Molecular Cloning of Dermaseptins B, A Family of Skin Peptide Antibiotics", The Journal of Biological Chemistry, 273(24): 14690-14697, 1998.
Chicharro et al. "N-Terminal Fatty Substitution Increases the Leishmanicidal Activity of CA(1-7)M(2-9), A Cecropin-Melittin Hybrid Peptide", Antimicrobial Agents and Chemotherapy, 45(9): 2441-2449, 2001.
Chu-Kung et al. "Promotion of Peptide Antimicrobial Activity by Fatty Acid Conjugation", Bioconjugate Chemistry, 15: 530-535, 2004.
Cohen "Epidemiology of Drug Resistance: Implications for a Post-Antimicrobial Era", Science, 257, 1050-1055, 1992.
Cosgrove et al. "The Impact of Antimicrobial Resistance on Health and Economic Outcomes", Clinical Infectious Diseases, 36: 1433-1437, 2003.

Darveau et al. "Beta-Lactam Antibiotics Potentiate Magainin 2 Antimicrobial Activity In Vitro and In Vivo", Antimicrobial Agents and Chemotherapy, 35(6): 1153-1159,1991.
De Lucca et al. "Fungicidal and Binding Properties of the Natural Peptides Cecropin B and Dermaseptin", Medical Mycology, 36: 291-298, 1998.
DeGray et al. "Expression of an Antimicrobial Peptide Via the Chloroplast Genome to Control Phytopathogenic Bacteria and Fungi", Plant Physiology, 127: 852-862, 2001.
Devine et al. "Cationic Peptides: Distribution and Mechanisms of Resistance", Current Pharmaceutical Design, 8: 703-714, 2002.
Doyle et al. "Synthesis of Potential Anti-HIV GP120 Inhibitors Using a Lysine Template", Journal of Enzyme Inhibition and Medicinal Chemistry, 17(3): 175-182, 2002.
Efron et al. "Direct Interaction of Dermaseptin S4 Aminoheptanoyl Derivative With Intraerythrocytic Malaria Parasite Leading to Increased Specific Antiparasitic Activity in Culture", The Journal of Biological Chemistry, 277(27): 24067-24072, 2002. p. 24068, Table 1, 1st Col.
Elsbach et al. "Role of the Bactericidal/Peremeability-Increasing Protein in Host Defence", Current Opinion in Immunology, 10: 45-49, 1998.
Epand "Biophysical Studies of Lipopeptide-Membrane Interactions", Biopolymers, 43: 15-24, 1997.
Epand et al. "Direct Comparison of Membrane Interactions of Model Peptides Composed of Only Leu and Lys Residues", Biopolymers (Peptide Science), 71: 2-16, 2003. p. 5, Table 1, p. 6, 2nd Paragraph.
Epand et al. "Diversity of Antimicrobial Peptides and Their Mechansims of Action", Biochimica et Biophysica Acta, 1462: 11-28, 1999.
Epand et al. "Mechanisms for the Modulation of Membrane Bilayer Properties by Amphipathic Helical Peptides", Biopolymers, 37(5): 319-338, 1995. Abstract.
Fahrner et al. "Solution Structure of Protegrin-1, A Broad-Spectrum Antimicrobial Peptide From Porcine Leukocytes", Chemistry & Biology, 3: 543-550, 1996.
Fritig et al. "Antimicrobial Proteins in Induced Plant Defense", Current Opinion in Immunology, 10: 16-22, 1998.
Gaidukov et al. "Analysis of Membrane-Binding Properties of Dermaseptin Analogues: Relationships Between Binding and Cytotoxicity", Biochemistry, 42: 12866-12874, 2003.
Gallo et al. "Antimicrobial Peptides: An Emerging Concept in Cutaneous Biology", Journal of Investigative Dermatology, 111: 739-743, 1998.
Gennaro et al. "Pro-Rich Antimicrobial Peptides From Animals: Structure, Biological Functions and Mechanism of Action", Current Pharmaceutical Design, 8: 763-778, 2002.
Ghosh et al. "Selective Cytotoxicity of Dermaseptin S3 Toward Intraerythrocytic *Plasmodium falciparum* and the Underlying Molecular Basis", The Journal of Biological Chemistry, 272(50): 31609-31616, 1997.
Giacometti et al. "Antiendotoxin Acitivity of Antimicrobial Peptides and Glycopeptides", Journal of Chemotherapy, 15(2): 129-133, 2003.
Giacometti et al. "In-Vitro Activity and Killing Effect of Polycationic Peptides on Methicillin-Resistant *Stapholoccus aureus* and Interactions With Clinically Used Antibiotics", Diagnostic Microbiology and Infectious Disease, 38: 115-118, 2000.
Gough et al. "Antiendotoxin Activity of Cationic Peptide Antimicrobial Agents", Infection and Immunity, 64(12): 4922-4927, 1996.
Gudmundsson et al. "Neutrophil Antibacterial Peptides, Multifunctional Effector Molecules in the Mammalian Immune System", Journal of Immunological Methods, 232: 45-54, 1999.
Hancock "Cationic Peptides: Effectors in Innate Immunity and Novel Antimicrobials", The Lancet Infectious Diseases, 1: 156-164, 2001.
Hancock et al. "Cationic Peptides: A New Source of Antibiotics", TIBTECH, Trends in Biotechnology, 16: 82-88, 1998.
Hancock et al. "Peptide Antibiotics", Antimicrobial Agents and Chemotherapy, 43(6): 1317-1323, 1999.
Hansen "Nisin as a Model Food Preservative", Critical Reviews in Food Sciences and Nutrition, 34(1): 69-93, 1994.
Haynie et al. "Antimicrobial Activities of Amphiphilic Peptides Covalently Bonded to a Water-Insoluble Resin", Antimicrobial Agents and Chemotherapy, 39(2): 301-307, 1995. Abstract, Table 1, p. 303.
Hernandez et al. "Functional and Structural Damage in *Leishmania mexicana* Exposed to the Cationic Peptide Dermaseptin", European Journal of Cell Biology, 59: 414-424, 1992.
Hoffmann et al. "*Drosophila* Innate Immunity: An Evolutionary Perspective", Nature Immunology, 3(2): 121-126, 2002.
Holmberg et al. "Health and Economic Impacts of Antimicrobial Resistance", Reviews of Infectious Diseases, 9(6): 1065-1078, 1987.
Hong et al. "Structure and Organization of Hemolytic and Nonhemolytic Diastereomers of Antimicrobial Peptides in Membranes", Biochemistry, 38: 16963-16973, 1999.
House of Lords "Resistance to Antibiotics and Other Antimicrobial Agents", The United Kingdom Parliament, Science and Technology—7th Report, HL Paper 81-11, Session 1997-1998.
Huang "Peptide-Lipid Interactions and Mechanisms of Antimicrobial Peptides", Novartis Found Symposium, 225: 188-200, 1999. Discussion 200-206.
Hwang et al. "Structure-Function Relationships of Antimicrobial Peptides", Biochemistry and Cell Biology, 76(2/3): 235-246, 1998.
Jacob et al. "Potential Therapeutic Applications of Magainins and Other Antimicrobial Agents of Animal Origin", Ciba Foundation Symposium, 186: 197-223, 1994.
Jing et al. "The Structure of the Antimicrobial Peptide Ac-RRW-WRF-NH2 Bound to Micelles and Its Interactions With Phospholipid Bilayers", Journal of Peptide Research, 61: 219-229, 2003. Abstract.
Johnson et al. "Engineering Increased Stability in the Antimicrobial Peptide Pediocin PA-1", Applied and Environmental Microbiology, 66(11): 4798-4802, 2000. Abstract, Fig.1, p. 4799.
Johnstone et al. "In Vitro Characterization of the Anticancer Activity of Membrane-Active Cationic Peptides. I. Peptide-Mediated Cytotoxicity and Peptide-Enhanced Cytotoxic Activity of Doxorubicin Against Wild-Type and P-Glycoprotein Over-Expressing Tumor Cell Lines" Anti-Cancer Drug Design, 15: 151-160, 2000.
Knight "Non-Oncologic Applications of Radiolabeled Peptides in Nuclear Medicine", The Quarterly Journal of Nuclear Medicine, 47: 279-291, 2003.
Kutner et al. "Characterization of Permeation Pathways in the Plasma Membrane of Human Erythrocytes Infected With Early Stages of *Plasmodium falciparum*: Association With Parasite Development", Journal of Cellular Physiology, 125: 521-527, 1985.
Lambros et al. "Synchronization of *Plasmodium falciparum* Erythocytic Stages in Culture", Journal of Parasitology, 65(3): 418-420, 1979.
Latham "Therapeutic Peptides Revisited", Nature Biotechnology, 17: 755-757, 1999.
Lee et al. "The Protective Effects of Lactoferrin Feeding Against Endotoxin Lethal Shock in Germfree Piglets", Infection and Immunity, 66(4): 1421-1426, 1998.
Lehrer et al. "Antimicrobial Peptides in Mammalian and Insect Host Defense", Current Opinion in Immunology, 11: 23-27, 1999.
Lehrer et al. "Defensins: Antimicrobial and Cytotoxic Peptides of Mammalian Cells", Annual Reviews in Immunology, 11: 105-128, 1993.
Levy "Antimicrobial Proteins and Peptides of Blood: Templates for Novel Antimicrobial Agents", Blood, 96: 2664-2672, 2000.
Lockwood et al. "Acylation of SC4 Dodecapeptide Increases Bactericidal Potency Against Gram-Positive Bacteria, Including Drug-Resistant Strains", Biochemical Journal, 378: 93-103, 2004.
Lupetti et al. "Radiolabelled Antimicrobial Peptides for Infection Detection", The Lancet Infectious Diseases, 3: 223-229, 2003.
Mak et al. "The Increases Bactericidal Activity of a Fatty Acid-Modified Synthetic Antimicrobial Peptide of Human Cathepsin G Correlates With Its Enhanced Capacity to Interact With Model Membranes", International Journal of Antimicrobial Agents, 21: 13-19, 2003.
Matsuzaki "Why and How Are Peptide-Lipid Interactions Utilized for Self-Defense? Magainins and Tachyplesins as Archetypes", Biochimica et Biophysica, 1462: 1-10, 1999.

Merrifield "Solid Phase Peptide Synthesis. I. The Synthesis of a Tetrapeptide", Journal of the American Chemical Society, 85: 2149-2154, 1963.

Moore et al. "Preliminary Experimental Anticancer Activity of Cecropins", Peptide Research, 7(5): 265-269, 1994.

Mor "Peptide-Based Antibiotics: A Potential Answer to Raging Antimicrobial Resistance", Drug Development Research, 50: 440-447, 2000.

Mor et al. "Antifungal Activity of Dermaseptin, a novel Vertebrate Skin Peptide", Journal de Mycologique Medicine, 1: 216-220, 1991.

Mor et al. "Isolation and Structure of Novel Defensive Peptides From Frog Skin", European Journal of Biochemistry, 219: 145-154, 1994.

Mor et al. "Isolation, Amino Acid Sequence, and Sunthesis of Dermaseptin, a Novel Antimicrobial Peptide of Amphibian Skin", Biochemistry, 30: 8824-8830, 1991.

Mor et al. "Structure, Synthesis, and Activity of Dermaseptin B, A Novel Vertebrate Defensive Peptide From Frog Skin: Relationship With Adenoregulin", Biochemistry, 33: 6642-6650, 1994.

Mor et al. "The NH2-Terminal Alpha-Helical Domain 1-18 of Dermaseptin Is Responsible for Antimicrobial Activity", The Journal of Biological Chemistry, 269(3): 1934-1939, 1994.

Mor et al. "The Vertebrate Peptide Antibiotics Dermaseptins Have Overlapping Structural Features but Target Specific Microorganisms", The Journal of Biological Chemistry, 269(50): 31635-31641, 1994.

Murphy et al. "Defensins are Mitogenic for Epithelial Cells and Fibroblasts", Journal of Cellular Physiology, 155: 408-413, 1993.

National Nosocomial Infections Surveillance "National Nosocomial Infections Surveillance (NNIS) Report, Data Summary From Oct. 1986-Apr. 1996, Isued May 1996. A Report From the National Nosocomial Infections Surveillance (NNIS) System", AJIC, American Journal of Infection Control, 24: 380-388, 1996.

National Nosocomial Infections Surveillance "National Nosocomial Infections Surveillance (NNIS) System Report, Data Summary From Jan. 1990-May 1999, Issued Jun. 1999", AJIC, American Journal of Infection Control, 27: 520-532, 1999.

Nicolas et al. "Peptides as Weapons Against Microorganisms in the Chemical Defense System of Vertebrates", Annual Reviews of Microbiology, 49: 277-304, 1995.

Nissen-Meyer et al. "Ribosomally Synthesized Antimicrobial Peptides: Their Function, Structure, Biogenesis, and Mechanism of Action", Archives in Microbiology, 167: 67-77, 1997.

Nizet et al. "Surviving Innate Immunity", Trends in Microbiology, 10(8): 358-359, 2002.

Oh et al. "Role of the Hinge Region and the Tryptophan Residue in the Synthetic Antimicrobial Peptides, Cecropin A(1-8)-Magainin 2(1-12) and Its Analogues, on Their Antibiotic Activities and Structures", Biochemistry, 39: 11855-11864, 2000.

Ono et al. "Design and Synthesis of Basic Peptides Having Amphipathic Beta-Structure and Their Interaction With Phospholipid Membranes", Biochimica et Biophysica Acta (BBA)—Biomembranes, 1022(2): 237-244, 1990. Abstract.

Osusky et al. "Transgenic Plants Expressing Cationic Peptide Chimeras Exhibit Broad-Spectrum Resistance to Phytopathogens", Nature Biotechnology, 18: 1162-1166, 2000.

Osusky et al. "Transgenic Potatoes Expressing a Novel Cationic Peptide Are Resistant to Late Blight and Pink Rot", Transgenic Research, 13: 181-190, 2004.

Pagagianni "Ribosomally Synthesized Peptides With Antimicrobial Properties: Biosynthesis, Structure, Function, and Applications", Biotechnology Advances, 21: 465-499, 2003.

Papo et al. "New Lytic Peptides Based on the D,L-Amphipathic Helix Motif Preferentially Kill Tumor Cells Compared to Normal Cells", Biochemistry, 42: 9346-9354, 2003.

Patrzykat et al. "Sublethal Concentrations of Pleurocidin-Derived Antimicrobial Peptides Inhibit Macromolecular Synthesis in *Escherichia coli*", Antimicrobial Agents and Chemotherapy, 46(3): 605-614, 2002.

Peggion et al. "Trichogin: A Paradigm for Lipopeptaibols", Journal of Peptide Science, 9: 679-689, 2003.

Peschel "How Do Bacteria Resist Human Antimicrobial Peptides?", Trends in Microbiology, 10(4): 179-186, 2002.

Piers et al. "The Interaction of a Recombinant Cecropin/Melittin Hybrid Peptide With the Outer Membrane of *Pseudomonas aeruginosa*", Molecular Microbiology, 12(6): 951-958, 1994.

Powell et al. "Design of Self-Processing Antimicrobial Peptides for Plant Protection", Letters in Applied Microbiology, 31: 163-168; 2000.

Rothbard et al. "Arginine-Rich Molecular Transporters for Drug Delivery: Role of Backbone Spacing in Cellular Uptake", Journal of Medicinal Chemistry, 45: 3612-3618, 2002.

Sahl et al. "Lantibiotics: Biosynthesis and Biological Activities of Uniquely Modified Peptides From Gram-Positive Bacteria", Annual Reviews in Microbiology, 52: 41-79, 1998.

Salzet "Antimicrobial Peptides Are Signaling Molecules", Trends in Immunology, 23(6): 283-284, 2002.

Scott et al. "An Alpha-Helical Cationic Antimicrobial Peptide Selectively Modulates Macrophage Responses to Lipopolysaccharide and Directly Alters Macrophage Gene Expression", The Journal of Immunology, 165: 3358-3365, 2000.

Scott et al. "The Human Antimicrobial Peptide LL-37 Is a Multifunctional Modulator of Innate Immune Responses", The Journal of immunology, 169: 3883-3891, 2002.

Shai "From Innate Immunity to De-Novo Designed Antimicrobial Peptides", Current Pharmaceutical Design, 8: 715-725, 2002.

Shai "Mode of Action of Membrane Active Antimicrobial Peptides", Biopolymers, 66: 236-248, 2002.

Shai "Molecular Recognition Between Membrane-Spanning Polypeptides", TIBS, Trends in Biochemical Science, 20: 460-464, 1995.

Shepherd et al. "Interactions of the Designed Antimicrobial Peptide MB21 and Truncated Dermaseptin S3 With Lipid Bilayers: Molecular-Dynamics Simulations", Biochemical Journal, 370: 233-243, 2003.

Simmaco et al. "Antimicrobial Peptides From Amphibian Skin: What Do Tehy Tell Us?", Biopolymers, 47: 435-450, 1998.

Stark et al. "Cationic Hydrophobic Peptides With Antimicrobial Activity", Antimicrobial Agents and Chemotherapy, 46(11): 3585-3590, 2002. Abstract, Table 2, p. 3587, p. 3586, Lines 17-22.

Tiozzo et al. "Wide-Spectrum Antibiotic Activity of Synthetic, Amphipathic Peptides", Biochemical and Biophysical Research Communications, 249: 202-206, 1998.

Toniolo et al. "Lipopeptaibols, A Novel Family of Membrane Active, Antimicrobial Peptides", CMLS, Cellular and Molecular Life Sciences, 58: 1179-1188, 2001.

Tossi et al. "Amphipathic, Alpha-Helical Antimicrobial Peptides", Biopolymers, 55(1): 4-30, 2000. Abstract, Table 1, p. 7-8, Table II, p. 13.

Tossi et al. "Molecular Diversity in Gene-Encoded, Cationic Antimicrobial Polypeptides", Current Pharmaceutical Design, 8: 743-761, 2002.

Vizioli et al. "Antimicrobial Peptides From Animals. Focus on Invertebrates", Trends in Pharmacological Sciences, 23(11): 494-496, 2002.

Wakabayashi et al. "N-Acylated and D Enantiomer Derivatives of a Nonamer Core Peptide of Lactoferricin B Showing Improved Antimicrobial Acitivity", Antimicrobial Ganets and Chemotherapy, 43(5): 1267-1269, 1999.

Wechselberger "Cloning of cDNAs Encoding New Peptides of the Dermaseptin-Family", Biochimica et Biophysica Acta, 1388: 279-283, 1998.

Welling et al. "Technetium-99m Labelled Antimicrobial Peptides Discriminate Between Bacterial Infections and Sterile Inflammations", European Journal of Nuclear Medicine, 27: 292-301, 2000.

Yang et al. "Crystallization of Antimicrobial Pores in Membranes: Magainin and Protegrin", Biophysical Journal, 79: 2002-2009, 2000.

Yaron et al. "Activity of Dermaseptin K4-S4 Against Foodborne Pathogens", Peptides, 24: 1815-1821, 2003. Abstract, Table 1, p. 817, p. 1819, Paragraph 1.

Yeaman et al. "Mechanisms of Antimicrobial Peptide Action and Resistance", Pharmacological Reviews, 55(1): 27-55, 2003.

Zasloff "Antimicrobial Peptides in Health and Disease", New England Journal of Medicine, 347(15): 1199-1200, 2002.

Zasloff "Antimicrobial Peptides of Multicellular Organisms", Nature, 415: 389-395, 2002.
Zasloff "Innate Immunity, Antimicrobial Peptides, and Protection of the Oral Cavity", The Lancet, 360: 1116-1117, 2002.
Zasloff et al. "Antimicrobial Activity of Synthetic Magainin Peptides and Several Analogues", Proc. Natl. Acad. Sci. USA, 85: 910-913, 1988.
Response Dated Feb. 4, 2010 to Official Action of Sep. 4, 2009 From the US Patent and Trademark Office Re.: U.S. Appl. No. 11/500,461.
Response Dated Dec. 23, 2009 to Office Action of Aug. 21, 2009 From the State Intellectual Property Office of the People's Republic of China Re.: Application No. 200580040186.2.
Official Action Dated Mar. 9, 2010 From the US Patent and Trademark Office Re.: U.S. Appl. No. 11/500,461.
Response Dated Mar. 29, 2011 to Official Action of Nov. 29, 2010 From the US Patent and Trademark Office Re.: U.S. Appl. No. 12/232,383.
Response Dated Jul. 8, 2010 to Official Action of Mar. 9, 2010 From the US Patent and Trademark Office Re.: U.S. Appl. No. 11/500,461.
Translation of Office Action Dated Jun. 4, 2010 From the State Intellectual Property Office of the People's Republic of China Re.: Application No. 200580040186.2.
Communication Pursuant to Article 94(3) EPC Dated Jul. 29, 2010 From the European Patent Office Re. Application No. 08738266.9.
Notice of Allowance Dated Nov. 8, 2010 From the US Patent and Trademark Office Re. U.S. Appl. No. 11/500,461.
Official Action Dated Nov. 29, 2010 From the US Patent and Trademark Office Re.: U.S. Appl. No. 12/232,383.
Response Dated Oct. 14, 2010 to Office Action of Jun. 4, 2010 From the State Intellectual Property Office of the People's Republic of China Re.: Application No. 200580040186.2.
Response Dated Nov. 28, 2010 to Communication Pursuant to Article 94(3) EPC of Jul. 29, 2010 From the European Patent Office Re. Application No. 08738266.9.
Response Dated Oct. 28, 2010 to Official Action of Jul. 30, 2010 From the US Patent and Trademark Office Re.: U.S. Appl. No. 11/500,461.
Translation of Office Action Dated Feb. 3, 2012 From the State Intellectual Property Office of the People's Republic of China Re.: Application No. 200580040186.2.
Response Dated Oct. 6, 2010 to Official Action of Sep. 8, 2010 From the US Patent and Trademark Office Re.: U.S. Appl. No. 12/232,383.
Response Dated Dec. 4, 2011 to Decision on Rejection of Aug. 1, 2011 From the State Intellectual Property Office of the People's Republic of China Re.: Application No. 200580040186.2.
Response Dated May 17, 2011 to Office Action of Jan. 4, 2011 From the State Intellectual Property Office of the People's Republic of China Re.: Application No. 200580040186.2.
Official Action Dated Jun. 8, 2011 From the US Patent and Trademark Office Re.: U.S. Appl. No. 12/232,383.
Office Action Dated Jul. 5, 2011 From the Israel Patent Office Re. Application No. 182247 and Its Translation Into English.
Translation of Notice of Reason for Rejection Dated Aug. 5, 2011 From the Japanese Patent Office Re. Application No. 2007-533055.
Official Action Dated Jul. 30, 2010 From the US Patent and Trademark Office Re.: U.S. Appl. No. 11/500,461.
Supplemental Response After Interview Dated Jul. 27, 2010 to Official Action of Mar. 9, 2010 From the US Patent and Trademark Office Re.: U.S. Appl. No. 11/500,461.
Restriction Official Action Dated Jan. 20, 2012 From the US Patent and Trademark Office Re. U.S. Appl. No. 12/598,057.
Restriction Official Action Dated Jun. 5, 2012 From the US Patent and Trademark Office Re. U.S. Appl. No. 12/451,179.
Communication Pursuant to Rules 70(2) and 70a(2) EPC and Reference to Rule 39(1) EPC Dated Jan. 21, 2013 From the European Patent Office Re. Application No. 12178655.2.
Restriction Official Action Dated Jan. 8, 2013 From the US Patent and Trademark Office Re. U.S. Appl. No. 13/314,288.
European Search Report and the European Search Opinion Dated Dec. 18, 2012 From the European Patent Office Re. Application No. 12178655.2.
Official Action Dated Sep. 26, 2012 From the US Patent and Trademark Office Re. U.S. Appl. No. 12/451,179.
National Cancer Institute "Cancer Drug Information: Drug Approved for Leukemia", National Cancer Institute, NCI, National Institute of Health, 4 P., Sep. 5, 2012.
Niederpr?m et al. "Inhibition of Steroid 5[Alpha]-Reductase Activity by Aliphatic Fatty Acids. Candidates for Chemoprevention of Prostate Cancer", Annals of the New York Academy of Sciences, p. 227-230, 1995.
Sigma-Aldrich "Amino Acids Reference Chart", Sigma-Aldrich, 5 P., 2011.
Official Action Dated Apr. 1, 2013 From the US Patent and Trademark Office Re. U.S. Appl. No. 13/314,288.

* cited by examiner

ANTIMICROBIAL AGENTS

RELATED APPLICATIONS

This Application is a National Phase of PCT Patent Application No. PCT/IL2008/000563 having International filing date of Apr. 28, 2008, which claims the benefit of U.S. Provisional Patent Application No. 60/924,087 filed on Apr. 30, 2007. The contents of the above Applications are all incorporated herein by reference.

FIELD AND BACKGROUND OF THE INVENTION

The present invention relates to novel antimicrobial agents and, more particularly, to a novel class of polymers which are designed to exert antimicrobial activity while being stable, non-toxic and avoiding development of resistance thereto. The present invention further relates to pharmaceutical compositions, medical devices and food preservatives containing such polymers and to methods of treating medical conditions associated with pathogenic microorganisms utilizing same.

Antibiotics, which are also referred to herein and in the art as antibacterial or antimicrobial agents, are natural substances of relatively small size in molecular terms, which are typically released by bacteria or fungi. These natural substances, as well as derivatives and/or modifications thereof, are used for many years as medications for treating infections caused by bacteria.

The advancements in the field of antimicrobial agents in general, and antibiotics in particular had transformed medical care and dramatically reduced illness and death from infectious diseases. However, over the decades, almost all the prominent infection-causing bacterial strains have developed resistance to antibiotics.

Antibiotic resistance can result in severe adverse outcomes, such as increased mortality, morbidity and medical care costs for patients suffering from common infections, once easily treatable with antibiotics [1-6] and therefore became one of the most recognized clinical problems of today's governmental, medicinal and pharmaceutical research (U.S. Congress, Office of Technology Assessment, *Impacts of Antibiotic-Resistant Bacteria, OTA-H-*629, Washington, D.C., U.S. Government Printing Office (1995); House of Lords, Science and Technology 7th Report: *Resistance to Antibiotics and Other Antimicrobial Agents*, HL Paper 81-II, session (1997-98); and *Interagency Task Force on Antimicrobial Resistance*, A Public Health Action Plan to Combat Antimicrobial Resistance. Part 1: Domestic issues).

Due to the limitations associated with the use of classical antibiotics, extensive studies have been focused on finding novel, efficient and non-resistance inducing antimicrobial/antibacterial agents.

Within these studies, a novel class of short, naturally occurring peptides, which exert outstanding antimicrobial/antibacterial activity, was uncovered. These peptides, which are known as antimicrobial peptides (AMPs), are derived from animal sources and constitute a large and diverse family of peptides, which may serve as effective antimicrobial agents against antibiotic-resistant microorganisms, as discussed in some recent reviews [7-12].

AMPs are now recognized to have an important role in the innate host defense. They display a large heterogeneity in primary and secondary structures but share common features such as amphiphatic character and net positive charge. These features appear to form the basis for their cytolytic function.

On top of the ribosomally synthesized antimicrobial peptides that have been identified and studied during the last 20 years, thousands of de-novo designed AMPs, were developed [13]. These de-novo designed peptides are comprised of artificially designed sequences and were produced by genetic engineering or by chemical peptide syntheses.

AMPs are attractive targets for bio-mimicry and peptidomimetic development, as reproduction of critical peptide biophysical characteristics in an unnatural, sequence-specific oligomer should presumably be sufficient to endow antibacterial efficacy, while circumventing the limitations associated with peptide pharmaceuticals [14].

One of the challenges in designing new antimicrobial peptides relies on developing peptidomimetics that would have high specificity toward bacterial or fungal cells, and consequently, would allow better understanding of the mechanism underlying the peptide lytic specificity, i.e., discrimination between cell membranes. Structure-activity relationships (SAR) studies on AMPs typically involve the systematic modification of naturally occurring molecules or the de-novo design of model peptidomimetics predicted to form amphiphatic alpha-helices or beta-sheets, and the determination of structure and activity via various approaches [13], as follows:

Antimicrobial peptides can act in synergy with classical antibiotics, probably by enabling access of antibiotics into the bacterial cell [15, 16]. Other potential uses include food preservation [17-20], imaging probes for detection of bacterial or fungal infection loci [21-23] and lining of medical/surgical devices [24].

However, while the potential of AMPs as new therapeutic agents is well recognized, the use of the presently known AMPs is limited by lack of adequate specificity, and optional systemic toxicity [25-27]. Thus, there is a clear need for developing new antimicrobial peptides with improved specificity and toxicity profile.

Moreover, although peptides are recognized as promising therapeutic and antimicrobial agents, their use is severely limited by their in vivo and ex vivo instability and by poor pharmacokinetics. Peptides and polypeptides are easily degraded in oxidative and acidic environments and therefore typically require intravenous administration (so as to avoid, e.g., degradation in the gastrointestinal tract). Peptides are further broken down in the blood system by proteolytic enzymes and are rapidly cleared from the circulation. Moreover, peptides are typically characterized by poor absorption after oral ingestion, in particular due to their relatively high molecular mass and/or the lack of specific transport systems. Furthermore, peptides are characterized by high solubility and therefore fail to cross biological barriers such as cell membranes and the blood brain barrier, but exhibit rapid excretion through the liver and kidneys. The therapeutic effect of peptides is further limited by the high flexibility thereof, which counteracts their receptor-affinity due to the steep entropy decrease upon binding and a considerable thermodynamic energy cost. In addition, peptides are heat and humidity sensitive and therefore their maintenance requires costly care, complex and inconvenient modes of administration, and high-cost of production and maintenance. The above disadvantages impede the use of peptides and polypeptides as efficient drugs and stimulate the quest for an alternative, which oftentimes involves peptidomimetic compounds.

Peptidomimetic compounds are modified polypeptides which are designed to have a superior stability, both in vivo and ex vivo, and yet at least the same receptor affinity, as compared with their parent peptides. In order to design efficacious peptidomimetics, an utmost detailed three-dimensional understanding of the interaction with the intended target is therefore required.

In conclusion, most of the presently known antimicrobial peptides and peptidomimetics are of limited utility as therapeutic agents despite their promising antimicrobial activity. The need for compounds which have AMP characteristics, and are devoid of the limitations associated with AMPs is still present, and the concept of providing chemically and metabolically-stable active compounds in order to achieve enhanced specificity and hence enhanced clinical selectivity has been widely recognized.

U.S. patent application Ser. Nos. 11/234,183 and 11/500,461 and WO 2006/035431, by the present assignee, which are incorporated by reference as if fully set forth herein, teach a novel class of antimicrobial polymers which were designed so as to circumvent the limitations associated with antimicrobial peptides, and which are composed of hydrophobic moieties and amino acids. The teachings of these patent applications show that in order to achieve an active antimicrobial agent devoid of the drawbacks of classical antibiotic agents, and those of AMPs, three key attributes of AMPs need to be maintained: a flexible structure, an amphiphatic character and a net positive charge. As successfully presented in these patent applications, these novel active antimicrobial polymers are achieved by the use of positively charged amino acids and the use of non-amino acid hydrophobic moieties, such as, fatty acids and the likes, which will not only achieve the desired amphiphatic trait and resolve the production and maintenance issues limiting the use of polypeptides as drugs, but also alleviate the sever limitations restricting the administration of polypeptides as drugs.

As further demonstrated in U.S. patent application Ser. Nos. 11/234,183 and 11/500,461 and WO 2006/035431, this newly developed class of polymers has been shown to exhibit high antimicrobial activity, low resistance induction, non-hemolyticity, resistibility to plasma proteases and high affinity to microbial membranes.

While the antimicrobial polymers taught in U.S. patent application Ser. Nos. 11/234,183 and 11/500,461 and WO 2006/035431 indeed exhibit the desired properties and were shown to overcome the limitations associated with common antimicrobial agents as well as AMPs, other polymers which are based on the characteristics discussed hereinabove, having yet different structural attributes can be designed and used advantageously as antimicrobial agents.

There is thus a widely recognized need for, and it would be highly advantageous to have, metabolically-stable, non-toxic and cost-effective antimicrobial agents devoid of the above limitations.

SUMMARY OF THE INVENTION

The present inventors have now designed and successfully prepared a new class of polymeric compounds, which are based on positively charged amino acid residues and hydrophobic moieties. These novel polymers were found highly efficient as selective antimicrobial agents, while being devoid of toxicity and resistance induction.

According to one aspect of the present invention there is provided a cyclic polymer which includes a plurality of amino acid residues, at least one hydrophobic moiety residue, at least one residue that has a first functional group and at least one residue that has second functional group, wherein at least one of hydrophobic moiety residues is being covalently linked to at least two amino acid residues via an amine group of one amino acid residue and via a carboxyl group of the other amino acid residue, and wherein the first functional group and the second functional group are covalently linked therebetween, thereby forming the cyclic polymer.

According to another aspect of the present invention there is provided a polymer having the general Formula II:

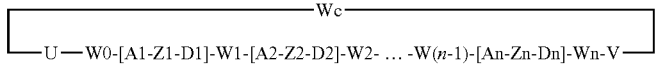

Formula II wherein:

n is an integer from 2 to 50;

$A_1, A_2, \ldots, An$ are each independently an amino acid residue;

$D_1, D_2, \ldots, Dn$ are each independently a hydrophobic moiety residue or absent, provided that at least one of the $D_1, D_2, \ldots, Dn$ is the hydrophobic moiety residue;

$Z_1, Z_2, \ldots, Zn$ and $W_1, W_2, \ldots, Wn-1$ are each independently a linking moiety linking two residues, the residues being selected from the group consisting of the amino acid residue and the hydrophobic moiety residue, or absent;

$W_0$ is a linking moiety linking one of the $A_1, Z_1$ and $D_1$ to U, or absent;

Wn is a linking moiety linking one of the An, Zn and Dn to V, or absent;

U is selected from the group consisting of a first functional group, an amino acid residue having the first functional group, a hydrophobic moiety residue having the first functional group, and a linking moiety having the first functional group or absent;

V is selected from the group consisting of a second functional group, an amino acid residue having the second functional group, a hydrophobic moiety residue having the second functional group, and a linking moiety having the second functional group or absent; and Wc is a cyclizing moiety.

According to yet another aspect of the present invention there is provided a linear polymer comprising a plurality of amino acid residues and at least one hydrophobic moiety residue, wherein at least one of the hydrophobic moiety residues is being covalently linked to at least two amino acid residues via an amine group in the side-chain of one amino acid residue and via a carboxyl group of the other amino acid residue.

According to further features in some embodiments of the invention described below, the first functional group is an amine group and the second functional group is a carboxyl group, or the first functional group is a carboxyl group and the second functional group is an amine group, the first functional group and the second functional group are covalently linked therebetween via a peptide bond.

According to still further features in the described embodiments the residue having the amine group as the first or the second functional group is an amino acid residue.

According to further features in the described embodiments the amine group is an N-alpha amine group.

According to still further features in the described embodiments the amine group forms a part of a side chain of the amino acid residue.

According to still further features in the described embodiments the residue having the amine group as the first or the second functional group is a hydrophobic moiety residue.

According to still further features in the described embodiments the residue having the carboxyl group as the first or the second functional group is an amino acid residue.

According to still further features in the described embodiments the carboxyl group is a C-alpha carboxyl group.

According to still further features in the described embodiments the residue having the carboxyl group as the first or the second functional group is a hydrophobic moiety residue.

According to still further features in the described embodiments the amine group in the side-chain of the one amino acid residue is an epsilon amine group of a lysine residue.

According to still further features in the described embodiments the polymer includes at least two hydrophobic moiety residues, wherein at least one of the hydrophobic moiety residues is being linked to the N-alpha of an amino acid residue at the N-terminus of the plurality of amino acid residues and/or the C-alpha of an amino acid residue at the C-terminus.

According to still further features in the described embodiments the polymer includes at least two hydrophobic moiety residues, wherein at least one of the hydrophobic moiety residues is being linked to the side-chain of an amino acid residue.

According to still further features in the described embodiments at least one of the amino acid residues has a hydrophobic moiety residue attached to a side chain thereof.

According to still further features in the described embodiments at least one of the amino acid residues is a positively charged amino acid residue. Preferably each of the amino acid residues is a positively charged amino acid residue.

According to still further features in the described embodiments the positively charged amino acid residue is selected from the group consisting of a histidine residue [His], a lysine residue [Lys], an ornithine residue [Orn] and an arginine residue [Arg]. Preferably the positively charged amino acid residues are a lysine residue.

According to still further features in the described embodiments at least one hydrophobic moiety residue is linked to at least one of the amino acid residues via a peptide bond. Preferably the hydrophobic moiety residue is linked to each of the amino acid residues via a peptide bond.

According to still further features in the described embodiments at least one of $W_1, W_2, \ldots, W_n$ and $Z_1, Z_2, \ldots, Z_n$ is a peptide bond. Preferably each of $W_1, W_2, \ldots, W_n$ and $Z_1, Z_2, \ldots, Z_n$ is a peptide bond.

According to still further features in the described embodiments at least one hydrophobic moiety has a carboxylic group at one end thereof and an amine group at the other end thereof.

According to still further features in the described embodiments the hydrophobic moiety is an ω-amino-fatty acid residue. Preferably the ω-amino-fatty acid residue is selected from the group consisting of 4-amino-butyric acid, 6-amino-caproic acid, 8-amino-caprylic acid, 10-amino-capric acid, 12-amino-lauric acid, 14-amino-myristic acid, 16-amino-palmitic acid, 18-amino-stearic acid, 18-amino-oleic acid, 16-amino-palmitoleic acid, 18-amino-linoleic acid, 18-amino-linolenic acid and 20-amino-arachidonic acid.

According to still further features in the described embodiments at least one of $D_1, D_2, \ldots, D_n$ is a ω-amino-fatty acid residue.

According to still further features in the described embodiments the plurality of amino acid residues comprises from 2 to 50 amino acid residues.

According to still further features in the described embodiments the polymer includes from 1 to 50 hydrophobic moiety residues.

According to still further features in the described embodiments the hydrophobic moiety residue includes at least one fatty acid residue. Preferably the fatty acid residue is selected from the group consisting of a butyric acid residue, a caprylic acid residue and a lauric acid residue.

According to still further features in the described embodiments the polymer further includes at least one active agent attached thereto.

According to still further features in the described embodiments the polymer is capable of delivering at least one active agent to at least a portion of the cells of a pathogenic microorganism.

According to still further features in the described embodiments the polymer has an antimicrobial activity.

According to still further features in the described embodiments the polymer is capable of selectively destructing at least a portion of the cells of a pathogenic microorganism.

According to yet an additional aspect of the present invention there is provided a pharmaceutical composition which includes, as an active ingredient, at least one of the polymers presented herein and a pharmaceutically acceptable carrier.

According to further features in preferred embodiments of the invention described below, the pharmaceutical composition is packaged in a packaging material and identified in print, in or on the packaging material, for use in the treatment of a medical condition associated with a pathogenic microorganism.

According to still further features in the described preferred embodiments, the pharmaceutical composition further includes at least one additional therapeutically active agent.

According to still an additional aspect of the present invention there is provided a method of treating a medical condition associated with a pathogenic microorganism, the method is effected by administering to a subject in need thereof a therapeutically effective amount of at least one of the polymers presented herein.

According to further features in the preferred embodiments of the invention described below, the method further includes administering to the subject at least one additional therapeutically active agent.

According to still further features in the described embodiments at least one of the additional therapeutically active agents is an antibiotic agent.

According to a further aspect of the present invention there is provided a medical device comprising the polymer presented herein and a delivery system configured to deliver the polymer to a bodily site of a subject.

According to yet a further aspect of the present invention there is provided a food preservative comprising an effective amount of at least one of the polymers presented herein.

According to still a further aspect of the present invention there is provided an imaging probe for detecting a pathogenic microorganism, the imaging probe includes a polymer according to the present embodiments, whereas the polymer further includes at least one labeling agent attached thereto.

The present invention successfully addresses the shortcomings of the presently known configurations by providing new antimicrobial polymers, which combine the merits of therapeutically active antimicrobial peptides, e.g., high efficacy and specificity, without exhibiting the disadvantages of peptides.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

DESCRIPTION OF THE PREFERRED EMBODIMENTS

The present invention is of new polymeric antimicrobial compounds, which are designed to exert antimicrobial activity while being stable, non-toxic and avoiding development of resistance thereto, and can therefore be beneficially utilized in the treatment of various medical conditions associated with pathogenic microorganisms. The present invention is further of pharmaceutical compositions, medical devices and food preservatives containing same. The antimicrobial polymers of the present invention preferably include one or more positively charged amino acid residues and one or hydrophobic moiety residues attached one to another.

The principles and operation of the present invention may be better understood with reference to the accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed above, the use of classical modern antibiotic agents such as tetracycline, gentamycin, ciprofloxacin and methicillin has become during the years severely limited by the development of resistance thereto. Extensive studies have therefore been conducted in a search for novel antimicrobial agents that would circumvent the resistance induction.

As further discussed above, naturally occurring antimicrobial peptides (AMPs) are exceptionally potent antimicrobial agents, but as pharmaceuticals they suffer from the limitations associated with peptide production, maintenance and modes of clinical administration for therapeutic use.

Based on the knowledge which accumulated over the years on the nature of antimicrobial peptides and the limitations associated with their use, the present inventors hypothesized that in order to achieve antimicrobial agents devoid of the resistance-inducing drawbacks of classical antibiotic agents, and those of AMPs, three key attributes of AMPs needs to be maintained: a flexible structure, an amphiphatic character and a net positive charge.

U.S. patent application Ser. Nos. 11/234,183 and 11/500, 461 and WO 2006/035431, by the present assignee, which are all incorporated herein by reference as if fully set forth herein, teach a novel class of antimicrobial polymeric agents which were designed to exert antimicrobial activity while being chemically and pharmaceutically stable, non-toxic and non-resistance inducing, as well as methods of preparing of these agents, pharmaceutical compositions containing same and a method of treating medical conditions associated with pathological microorganisms. These antimicrobial polymeric agents were shown to be non-hemolyticity and to exhibit resistibility to plasma proteases.

The antimicrobial polymers taught in U.S. patent application Ser. Nos. 11/234,183 and 11/500,461 and WO 2006/035431 are linear polymers, as defined herein, which comprise a plurality of amino acid residues, preferably positively charged amino acid residues and hydrophobic moieties that are linked to two amino acid residues via the N-alpha amine of one amino acid residue and the C-alpha carboxyl of another amino acid residue. Preferred hydrophobic moieties include fatty acids and particularly co-amino fatty acids.

Structure-Activity relationship (SAR) studies have been conducted using extensive series of polymers against a variety of microorganisms in order to determine the effect of features such as charge and hydrophobicity of the polymers on their antimicrobial activity. Some of the conclusions which rose from these studies indicated that while positive charge has an effect on the activity, the hydrophobicity is a more sensitive feature, and even more the choice of hydrophobic moiety, such that, for example, lengthening of the hydrocarbon chain, increases the activity.

While further exploring various structural features that may affect the activity of the polymers presented in U.S. patent application Ser. Nos. 11/234,183 and 11/500,461 and WO 2006/035431, the present inventors have designed and successfully prepared and practiced novel polymers, which are also based on amino acid residues and hydrophobic moiety residues, but into which novel structural features have been introduced and studied. Thus, the effect of rigidifying the polymer structure by means of cyclic polymers was studied. Further, the use of available functional groups in side-chains of some amino-acids in the polymer was studied.

It was hypothesized that the use of non-linear polypeptide structure and the use of available functional groups in side-chains of some amino-acids would further improve the production and maintenance issues limiting the use of polypeptides as drugs, and would also contribute to the alleviation of the sever limitations restricting the administration of polypeptides as drugs. Thus, it was envisioned that cyclization of the polymers and polymerization via amino-acid functional groups other than the N-alpha and/or C-alpha thereof may improve the desired activity of the polymers.

As demonstrated in the Examples section that follows, it has been found that cyclic polymers exhibit an improvement in their antimicrobial activity as compared to their linear counterparts.

Thus, according to one aspect of the present invention, there is provided a cyclic polymer, having an antimicrobial activity, which comprises a plurality (e.g., two or more) of amino acid residues and one or more hydrophobic moiety residues, and further comprising a first functional group which forms a part of one residue and a second functional group which forms a part of another residue, wherein at least one of the hydrophobic moiety residues is covalently linked to at least two amino acid residues via an amine group of one amino acid residue and/or via a carboxyl group of the other amino acid residue, and wherein the first functional group and second functional group are covalently linked therebetween. Therefore, the polymer is a cyclized chain made of a sequence of amino acid residues, interrupted by one or more hydrophobic moiety residues.

The present embodiments further encompass any enantiomers, prodrugs, solvates, hydrates and/or pharmaceutically acceptable salts of the polymers described herein.

As used herein, the term "enantiomer" refers to a stereoisomer of a polymer that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The term "prodrug" refers to an agent, which is converted into the active polymer (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the polymer of the present embodiments) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The phrase "pharmaceutically acceptable salt" refers to a charged species of the parent polymer and its counter ion, which is typically used to modify the solubility characteristics of the parent compound and/or to reduce any significant irritation to an organism by the parent polymer, while not abrogating the biological activity and properties of the administered polymer. An example, without limitation, of a pharmaceutically acceptable salt would be a carboxylate anion and a cation such as, but not limited to, ammonium, sodium, potassium and the like.

The term "cyclic" as used herein in the context of the polymer, refers to a polymer that comprises an intramolecular covalent bond between two non-adjacent residues (monomers) therein, forming a cyclic polymer ring.

As is well accepted in the art in the molecular context, the term "residue", as used herein, refers to a portion, and typically a major portion of a molecular entity, such as molecule or a part of a molecule such as a group, which has underwent a chemical reaction and is now covalently linked to another molecular entity. In the context of the present invention, a residue is an equivalent term to a monomer comprising the polymer. For example, the molecular entity can be an amino acid molecule, and the portion of the amino acid which forms a part of a polypeptide chain (a polymer) after the formation of the polypeptide chain, is an amino acid residue (a monomer). An amino acid residue is therefore that part of an amino acid which is present in a peptide sequence upon reaction of, for example, an alpha-amine group thereof with a carboxylic group of an adjacent amino acid in the peptide sequence, to form a peptide amide bond and/or of an alpha-carboxylic acid group thereof with an alpha-amine group of an adjacent amino acid in the peptide sequence, to form a peptide amide bond. Similarly, the term "residue" refers to the major part of a hydrophobic moiety, such as, for example the acyl part of a fatty acid.

In the context of the present embodiments the polymer comprises residues of amino acids and hydrophobic moieties which constitute the monomers of the polymer. The term residue is meant to encompass other chemical moieties which form a part of the polymer, and which do not fall under the definition of amino acid or hydrophobic moiety, as these are defined herein. For example, the cyclic polymer may be "closed" or cyclized by means of a multifunctional or bifunctional moiety that will form a part of the cyclic polymer once it is cyclized.

As used herein throughout the term "amino acid" or "amino acids" is understood to include the 20 genetically coded amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids and other non-naturally occurring amino acids.

Tables 1 and 2 below list the genetically encoded amino acids (Table 1) and non-limiting examples of non-conventional/modified amino acids (Table 2) which can be used with the present invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Iie | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 2

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| Cyclohexylalanine | Chexa |
| Cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D/L-ornithine | D/Lorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |

TABLE 2-continued

| Non-conventional amino acid | Code |
|---|---|
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-α-methylalnine | Dnmala |
| D-α-methylarginine | Dnmarg |
| D-α-methylasparagine | Dnmasn |
| D-α-methylasparatate | Dnmasp |
| D-α-methylcysteine | Dnmcys |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | mser |
| L-α-methylvaline | Mtrp |
| L-α-methylleucine | Mval |
|  | Nnbhm |
| N-(N-(2,2-diphenylethyl)carbamylmethylglycine | Nnbhm |
| 1-carboxy-1-(2,2-diphenylethylamino)cyclopropane | Nmbc |
| N-(N-(3,3-diphenylpropyl)carbamylmethyl(1)glycine | Nnbhe |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcyclopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-a-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cyclododeclglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylserine | Dnmser |
| D-N-methylthreonine | Dnmthr |
| N-(1-methylethyl)glycine | Nva |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomo phenylalanine | Mhphe |
| N-(2-methylthioethyl)glycine | Nmet |
| N-(3-guanidinopropyl)glycine | Narg |

TABLE 2-continued

| Non-conventional amino acid | Code |
| --- | --- |
| N-(1-hydroxyethyl)glycine | Nthr |
| N-(hydroxyethyl)glycine | Nser |
| N-(imidazolylethyl)glycine | Nhis |
| N-(3-indolylethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| D/L-citrulline | D/Lctr |

As used herein, the phrase "moiety" describes a part, and preferably a major part of a chemical entity or compound, which typically has certain functionality or distinguishing features.

As used herein, the phrase "hydrophobic moiety" describes a chemical moiety that has a minor or no affinity to water, that is, which has a low or no dissolvability in water and often in other polar solvents. Exemplary suitable hydrophobic moieties for use in the context of the present embodiments, include, without limitation, hydrophobic moieties that consist predominantly of one or more hydrocarbon chains and/or aromatic rings, and one or more functional groups which may be non-hydrophobic, but do not alter the overall hydrophobicity of the hydrophobic moiety. Representative examples include, without limitation, fatty acids, hydrophobic amino acids (amino acids with hydrophobic side-chains), alkanes, alkenes, aryls and the likes, as these terms are defined herein, and any combination thereof.

As used herein, the phrase "functional group" describes a chemical group that is capable of undergoing a chemical reaction that typically leads to a bond formation. The bond, according to the present embodiments, is preferably a covalent bond. Chemical reactions that lead to a bond formation include, for example, nucleophilic and electrophilic substitutions, nucleophilic and electrophilic addition reactions, addition-elimination reactions, cycloaddition reactions, rearrangement reactions and any other known organic reactions that involve a functional group.

The first and second functional groups may form a part of an amino acid residue and/or a hydrophobic moiety residue in the polymer, or any other element in the polymer which does not fall under the definition of amino acid or hydrophobic moiety, such as, for example, a linking moiety. The first and second functional groups are selected such that they are capable of forming a covalent bond therebetween or therefrom. For example, either the first or the second functional group can be a binding pair of an amine and a carboxyl which form an amide (peptide bond), a hydroxyl and a carboxyl which form an ester, or a an amine and an aldehyde which form an imine (Schiff base).

According to some embodiments, the first functional group is an amine group and the second functional group is a carboxyl group. Alternatively, the first functional group is a carboxyl group and the second functional group is an amine group. Therefore the first functional group and the second functional group can form a peptide bond therebetween.

The amine group, in the context of the first and/or second functional group, can originate from an N-alpha amine of an amino acid residue, or from an amine on the side-chain of an amino acid residue, such as found for example, in lysine and ornithine. Alternatively, the amine can stem from a hydrophobic moiety residue, such as, for example, an amino-fatty acid. Similarly, the carboxyl group, in the context of the first and/or second functional group, can originate from a C-alpha carboxyl of an amino acid residue, or from a carboxyl on the side-chain of an amino acid residue, such as found for example, in aspartic acid and glutamic acid. Alternatively, the amine can stem from a hydrophobic moiety residue, such as, for example, an amino-fatty acid. Similarly, the carboxyl group can stem from a hydrophobic moiety residue, such as, for example, any fatty acid.

Preferably, the one of the first or second functional groups is an amine on a hydrophobic moiety residue, and the other functional group is a carboxyl on an amino acid residue.

As used herein, the term "amine" describes a —NR'R" group where each of R' and R" is independently hydrogen, alkyl, cycloalkyl, heteroalicyclic, aryl or heteroaryl, as these terms are defined herein.

As used herein, the term "alkyl" describes an aliphatic hydrocarbon including straight chain and branched chain groups. Preferably, the alkyl group has 1 to 20 carbon atoms, and more preferably 1-10 carbon atoms. Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. The alkyl can be substituted or unsubstituted. When substituted, the substituent can be, for example, an alkyl, an alkenyl, an alkynyl, a cycloalkyl, an aryl, a heteroaryl, a halide, a hydroxy, an alkoxy and a hydroxyalkyl as these terms are defined hereinbelow. The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "carboxyl", as used herein, refers to a —C(=O)—O—R', where R' is as defined herein. When R' is hydrogen the carboxyl group is referred to as a carboxylic acid, and when R' is an alkyl, the carboxyl group is referred to as an ester.

The term "amide" describes a —NR'—C(=O)— group, a —NR'—C(=O)—R" group or a —C(=O)—NR'R" group, wherein R' is as defined herein and R" is as defined for R'. An amide is used herein interchangeably with peptide bond.

The term "hydroxyl", as used herein, refers to an —OH group.

As used herein, the term "aldehyde" refers to a —C(=O)H group.

The term "imine", which is also referred to in the art interchangeably as "Schiff-base", describes a —N=CR'— group, with R' as defined herein. As is well known in the art, Schiff bases are typically formed by reacting an aldehyde and an amine-containing moiety such as amine, hydrazine, hydrazide and the like, as these terms are defined herein.

According to another aspect of the present invention, there is provided a linear polymer, having an antimicrobial activity, which comprises a plurality of amino acid residues and one or more hydrophobic moiety residues, wherein at least one of the hydrophobic moiety residues is being covalently linked to at least two amino acid residues via an amine group in the side-chain of one amino acid residue and via a carboxyl group of another amino acid residue.

The term "linear" as used herein in the context of the polymers, refers to a non-cyclic polymer, i.e., a polymer which have two termini and its backbone or amino-acid side-chains do not form a closed ring.

The term "side-chain", as used herein with reference to amino acids, refers to a chemical group which is attached to the α-carbon atom of an amino acid. The side-chain is unique for each type of amino acid and typically does not take part in forming the peptide bond in a naturally occurring protein or polypeptide, but can be used to form a link between monomers in the polymer presented herein in cases the side-chain comprises a suitable functional group. For example, the side chain for lysine can be regarded as an amino-butyl, e.g., an available amine group. For the specific side chains of all amino acids reference is made to A. L. Lehninger's text on Biochemistry (see, chapter 4).

According to some embodiments, the amine group in the side-chain of the amino acid residue is the epsilon amine group of a lysine residue.

Either the cyclic or the linear polymer, according to the present embodiments, may have two or more hydrophobic moiety residues, whereby at least one is linked to one amino acid at one end and to another amino acid residue at another end, and another may elongate the polymeric chain by being linked to either one of the termini thereof, for example to the N-alpha of a terminal amino acid residue and/or the C-alpha of a terminal amino acid residue. Optionally, a second hydrophobic moiety may be linked to a side-chain of an amino acid residue in the polymer.

Either the cyclic or the linear polymer, according to the present embodiments, includes from 2 to 50 amino acid residues. Alternatively, the polymer includes from 2 to 12 amino acid residues, and further alternatively from 4 to 8 amino acid residues and or from 5 to 7 amino acid residues.

The net positive charge of the polymer is maintained by having one or more positively charged amino acid residues in either the cyclic or the linear polymer, optionally in addition to the positively charged N-terminus amine.

In one exemplary embodiment of the present invention, all the amino acid residues in either the cyclic or the linear polymer are positively charged amino acid residues. An exemplary polymer according to this embodiment includes a plurality of lysine residues.

As used herein the phrase "positively charged amino acid" describes a hydrophilic amino acid with a side chain pKa value of greater than 7, namely a basic amino acid. Basic amino acids typically have positively charged side chains at physiological pH due to association with a hydronium ion. Naturally occurring (genetically encoded) basic amino acids include lysine (Lys, K), arginine (Arg, R) and histidine (His, H), while non-natural (non-genetically encoded, or non-standard) basic amino acids include, for example, ornithine, 2,3,-diaminopropionic acid, 2,4-diaminobutyric acid, 2,5,6-tri-aminohexanoic acid, 2-amino-4-guanidinobutanoic acid, and homoarginine.

In one embodiment of the present invention, each of the components in either the cyclic or the linear polymer according to the present embodiments is optionally linked to the other by a peptide bond.

The term "peptide bond" as used herein refers to an amide group, namely, a —(C=O)NH— group, which is typically formed by a nucleophilic addition-elimination reaction between a carboxylic group and an amine group, as these terms are defined herein.

However, either the cyclic or the linear polymers of the present embodiments may have other bonds linking the various components in the polymeric structure. Such non-peptidic bonds may render the polymer more stable while in a body or more capable of penetrating into cells. Thus, peptide bonds (—(C=O)NH—) within the polymer may be replaced, for example, by N-methylated amide bonds (—(C=O)NCH$_3$—), ester bonds (—C(R)H—C(=O)—O—C(R)—N—), ketomethylen bonds (—C(=O)CH$_2$—), aza bonds (—NH—N(R)—C(=O)—), wherein R is any alkyl, e.g., methyl, carba bonds (—CH$_2$—NH—), hydroxyethylene bonds (—CH(OH)—CH$_2$—), thioamide bonds (—CS—NH—), olefinic double bonds (—CH=CH—), retro amide bonds (—NH—(C=O)—), peptide derivatives (—N(R)—CH$_2$—C(=O)—), wherein R is the "normal" side chain, naturally presented on the carbon atom. These modifications can occur at any of the bonds along the polymer chain and even several (2-3) at the same time.

In an exemplary embodiment, all of the bonds in either the cyclic or the linear polymer, linking the amino acid residues and hydrophobic moiety residues to each other, are peptide bonds. For example, in one embodiment, the polymer is made of an amino acid residue linked by a peptide bond to a hydrophobic moiety residue which in turn is linked to a second amino acid residue by another peptide bond. In another example, the polymer of the previous example is elongated by a second hydrophobic moiety residue which is linked to a functional group in a side-chain of an amino acid residue, or to any one of the N- or C-termini, by a peptide bond, etcetera.

Either the cyclic or the linear polymer, according to the present embodiments, comprises from 1 to 50 hydrophobic moiety residues. Alternatively, the polymer comprises from 1 to 12 hydrophobic moiety residues, and further alternatively from 4 to 10 hydrophobic moiety residues or from 6 to 8 hydrophobic moiety residues.

The hydrophobic moieties that are used in the context of this and other aspects of the present invention have one or more hydrocarbon chains, and are capable of linking to one or two other components in the polymer (e.g., one or two of an amino acid residue and another hydrophobic moiety) via two peptide bonds. These moieties therefore have a carboxylic group at one end of the hydrocarbon chain (for linking a free amine group) and an amine group at the other (for linking a carboxylic acid group).

The hydrocarbon chain connecting the carboxylic and amine groups in such a hydrophobic moiety has from 4 to 30 carbon atoms.

In an exemplary embodiment of the present invention, the hydrophobic moiety residue is a fatty acid residue wherein the hydrocarbon chain can be unbranched and saturated, branched and saturated, unbranched and unsaturated or branched and unsaturated. Alternatively the hydrocarbon chain of the fatty acid residue is an unbranched and saturated chain having from 4 to 30 carbon atoms, or from 4 to 20 carbon atoms. Non-limiting example of such fatty acid residues are butyric acid residue, caprylic acid residue and lauric acid residue.

In another exemplary embodiment, the fatty acid residue has an amine on the distal carbon of the hydrocarbon chain (with respect to the carboxylic acid group). Such a fatty acid residue is referred to herein as an ω-amino fatty acid residue. Again here the hydrocarbon chain of the ω-amino fatty acid residue may have from 4 to 30 carbon atoms.

Non-limiting example of such ω-amino fatty acids are 4-amino-butyric acid, 6-amino-caproic acid, 8-amino-caprylic acid, 10-amino-capric acid, 12-amino-lauric acid, 14-amino-myristic acid, 16-amino-palmitic acid, 18-amino-stearic acid, 18-amino-oleic acid, 16-amino-palmitoleic acid, 18-amino-linoleic acid, 18-amino-linolenic acid and 20-amino-arachidonic acid.

According to an exemplary embodiment of the present invention, the hydrophobic moiety is selected from the group consisting of 4-amino-butyric acid, 8-amino-caprylic acid and 12-amino-lauric acid or is 8-amino-caprylic acid and 12-amino-lauric acid.

The cyclic polymers described herein can be collectively represented by the following general formula II:

The moieties which close the polymer into a cyclic polymer, denoted U and V, may each independently be absent or be an amino acid residue or a hydrophobic moiety residue, provided they each has a functional group, referred to hereinabove as the first and second functional groups, which can form a covalent bond therebetween. Thus, such amino acid residues and/or hydrophobic moiety residues can form together a unique linking moiety denoted herein as Wc, which is referred to herein as the cyclizing moiety.

As used herein, the phrase "linking moiety" describes a chemical moiety, group or a bond, as defined herein, which links between two residues or monomers. The linking moiety can thus be, for example, formed upon reacting two functional groups, each forms a part of another monomer or residue, thus linking the two monomers or residues. For example, an amine group on one monomer can form a peptide bond with a carboxyl group on another monomer and the resulting moiety is a peptide bond linking moiety.

According to exemplary embodiments at least one of the linking moieties in the polymers presented herein is a peptide bond, and alternatively all the linking moieties are peptide bonds.

The phrase "cyclizing moiety", denoted Wc in Formula II, refers to a chemical moiety which is formed when two residues in Formula II are linked therebetween, thereby forming

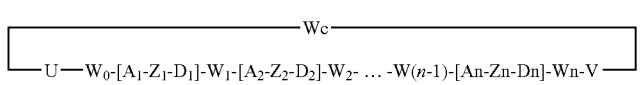

Formula II wherein:

n is an integer from 2 to 50, or from 2 to 12 or from 2 to 8;

$A_1, A_2, \ldots, An$ are each independently an amino acid residue, and according to exemplary embodiments a positively charged amino acid residue, and further alternatively all of $A_1, A_2, \ldots, An$ are positively charged amino acid residues as discussed hereinabove, such as histidine residues, lysine residues, ornithine residues and arginine residues, and further alternatively all the positively charged amino acid residues are lysine residues;

$D_1, D_2, \ldots, Dn$ are each independently a hydrophobic moiety residue, as defined and discussed hereinabove, or absent, provided that at least one such hydrophobic moiety residue exists in the polymer, preferably at least one of the hydrophobic moiety residues is a ω-amino-fatty acid residue;

Connecting each monomer of the residue are linking moieties, denoted $Z_1, Z_2, \ldots, Zn$ and $W_1, W_2, \ldots, Wn-1$, each of which independently linking an amino acid residue and a hydrophobic moiety residue or absent.

U is selected from the group consisting of the first functional group, as defined hereinabove, an amino acid residue having that first functional group, a hydrophobic moiety residue having that first functional group, and a linking moiety having that first functional group, or absent.

Similarly, V is selected from the group consisting of the second functional group, an amino acid residue having that second functional group, a hydrophobic moiety residue having that second functional group, and a linking moiety having that second functional group, or absent.

The linking moiety $W_0$ is linking any one of $A_1, Z_1$ and $D_1$ to U, or absent, and the linking moiety Wn is linking any one of An, Zn and Dn to V, or absent;

Wc is a cyclizing moiety.

the cyclic polymer. The cyclizing moiety may be, for example, a bond which is formed between two functional groups, such as, for a non-limiting example, an amide (peptide bond), a carboxylate (ester), a carbamate, an ether and the likes.

The two functional groups which form Wc, can stem from U and V, $W_0$ and Wn, or $A_1, Z_1$ and $D_1$ and An, Zn or Dn, or any combination thereof. Alternatively, the cyclizing moiety may comprise a residue of a multifunctional (as at least bifunctional) moiety which forms bonds with functional groups on U and V, $W_0$ and Wn, or $A_1, Z_1$ and $D_1$ and An, Zn or Dn, such as, for a non-limiting example, p-aminobenzoic acid or ethyleneglycol.

Preferably the cyclizing moiety, denoted Wc, is a peptide bond which is formed from an amine group on either U of V, and a carboxyl on either V or U.

Hence, for better clarity, the phrase "cyclic polymer" as used herein in the context of the polymer, refers to a polymer that comprises an intramolecular covalent bond which forms a part of a cyclizing moiety. The cyclizing moiety is positioned between two non-adjacent residues therein, forming a cyclic polymer ring that comprises at least two amino acid residues, at least one hydrophobic moiety residue, a cyclizing moiety and optionally further comprise a plurality of linking moieties and other residues. The cyclizing moiety may connect backbone to any two residues in the polymer via backbone atoms, side-chain atoms or a combination thereof.

According to exemplary embodiments, the cyclic polymers are polymers in which n is an integer from 2 to 5, the amino acid residues are all lysine residues, and the hydrophobic moiety residues are all 12-amino-lauric acid residues.

In particular embodiments the cyclic polymers are those having the Formulae hereinbelow:
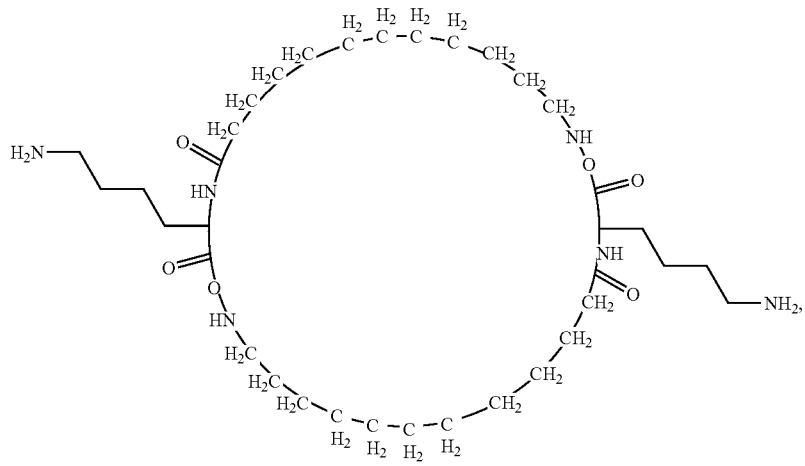
which is also referred to herein as Cyclic-$(NC_{12}K)_2$;
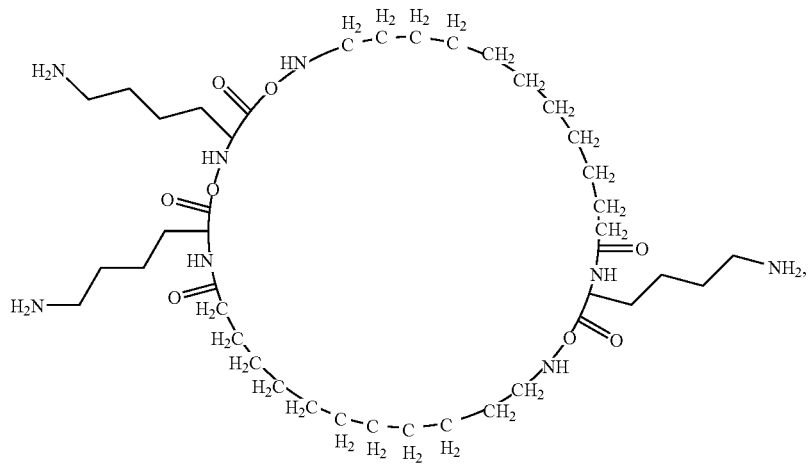
which is also referred to herein as Cyclic-$NC_{12}KKNC_{12}K$;
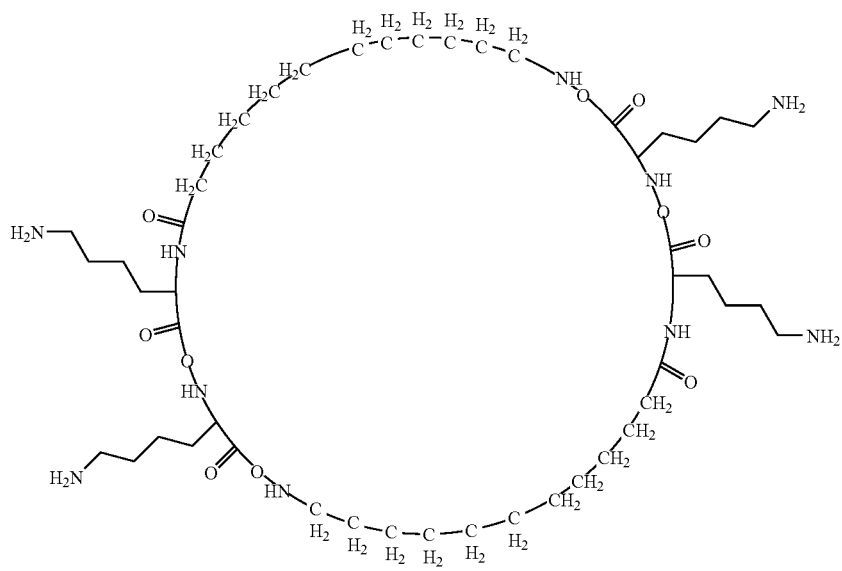

which is also referred to herein as Cyclic-(KNC$_{12}$K)$_2$; and

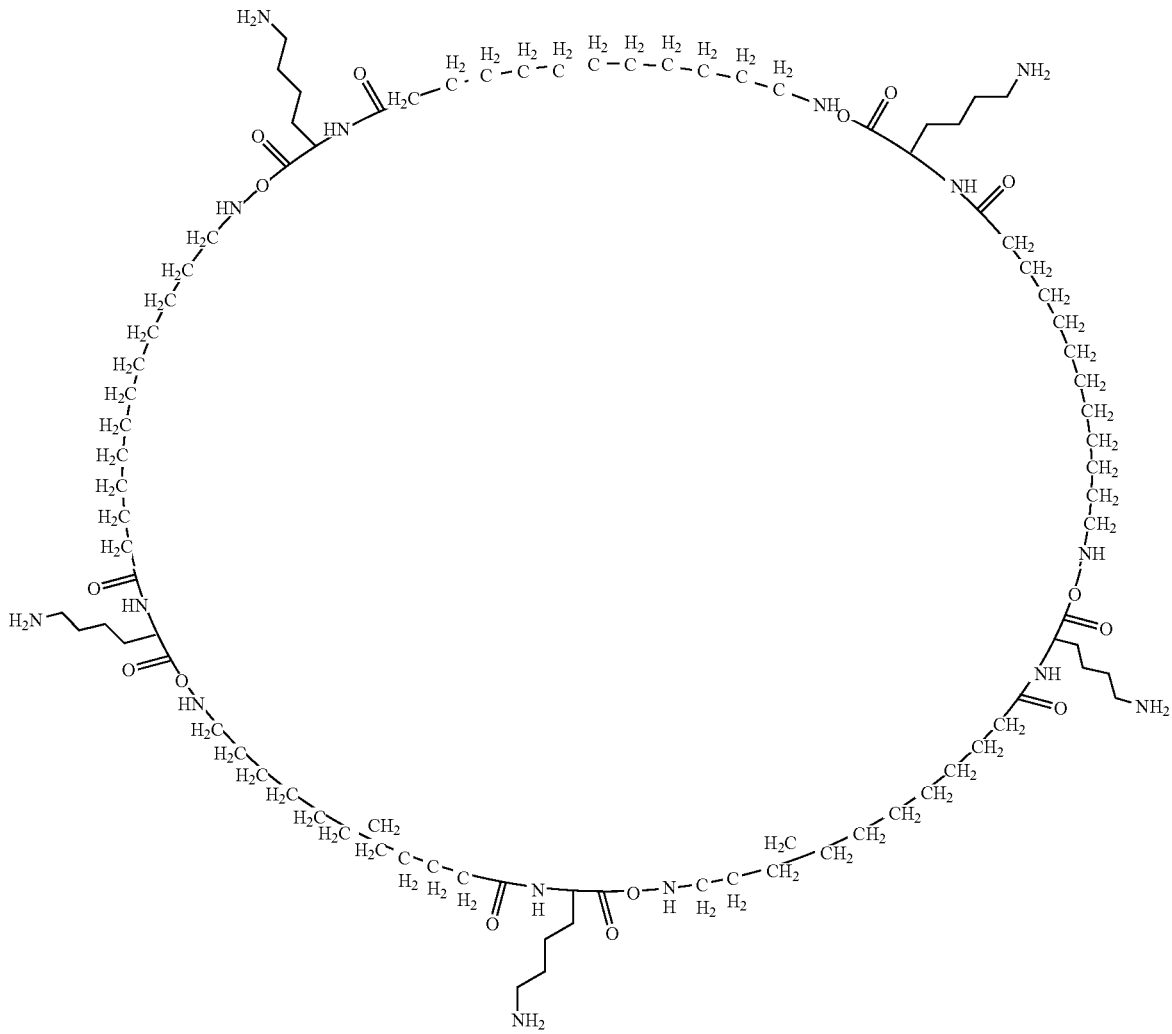

which is also referred to herein as Cyclic-(NC$_{12}$K)$_5$.

As discussed above, one or more of the hydrophobic moiety residues may be attached to a side chain of one or more of the amino acid residues of the polymer, i.e., act as a branch of the main cyclic polymer.

The linear polymers described herein can be collectively represented by the following general formula I:

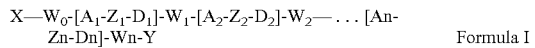

Formula I wherein:

n is an integer from 2 to 50, or from 2 to 12 or from 2 to 8;

$A_1, A_2, \ldots, An$ are each independently an amino acid residue, providing that at least one of $A_1, A_2, \ldots, An$ is linked to a hydrophobic moiety residue in the polymer via a functional group in its side-chain. $A_1, A_2, \ldots, An$ are preferably a positively charged amino acid residue, more preferably all of $A_1, A_2, \ldots, An$ are positively charged amino acid residues as discussed hereinabove, such as histidine residues, lysine residues, ornithine residues and arginine residues, and most preferably all the positively charged amino acid residues are lysine residues;

$D_1, D_2, \ldots, Dn$ are each independently a hydrophobic moiety residue, as defined and discussed hereinabove, or absent, provided that at least one such hydrophobic moiety residue exists in the polymer, preferably at least one of the hydrophobic moiety residues is a ω-amino-fatty acid residue;

Connecting each monomer of the residue are linking moieties, denoted $Z_1, Z_2, \ldots, Zn$ and $W_0, W_1, W_2, \ldots, Wn$, each of which independently linking an amino acid residue and a hydrophobic moiety residue or absent, preferably at least one of the linking moieties is a peptide bond and most preferable all the linking moieties are peptide bonds;

The fringes of the polymer, denoted X and Y, may each independently be hydrogen, a functional group (e.g., amine and/or carboxyl groups), a linking moiety, an amino acid residue, a hydrophobic moiety residue, another polymer having the general Formula I or absent.

As discussed above, one or more of the hydrophobic moiety residues may be attached to a side chain of one or more of the amino acid residues of the polymer which does not take part in, i.e., act as a branch of the main polymer.

Particularly preferred linear polymers according to the present embodiments are those having the Formula hereinbelow:

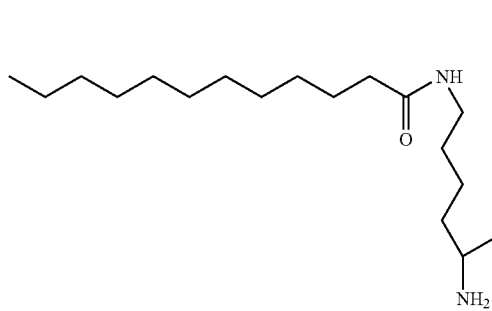 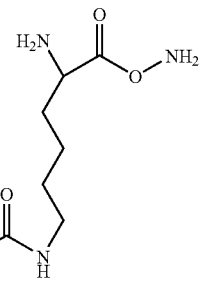

which is also referred to herein as $C_{12}K(\epsilon)NC_{12}K(\epsilon)NH_2$.

As in the case of the cyclic polymers discussed above, one or more of the hydrophobic moiety residues in the linear polymer may be attached to a side chain of one or more of the amino acid residues of the polymer, i.e., act as a branch of the main linear polymer.

Both the cyclic and the linear polymers according to the present embodiments can be readily synthesized as demonstrated for other antimicrobial polymers in U.S. patent application Ser. Nos. 11/234,183 and 11/500,461 and WO 2006/035431, in U.S. Provisional Patent Application 60/924,088, by the present assignee, and entitled "Anticancerous Polymeric Agents", which is co-filed with the instant application, and in the Examples section that follows hereinbelow. For example, polymers in which the linking moieties are peptide bonds, and hence resemble natural and synthetic peptides in this respect, can be prepared by classical methods known in the art for peptide syntheses. Such methods include, for example, standard solid phase techniques. The standard methods include exclusive solid phase synthesis, partial solid phase synthesis methods, fragment condensation, classical solution synthesis, and even by recombinant DNA technology. See, e.g., Merrifield, J. Am. Chem. Soc., 85:2149 (1963), incorporated herein by reference. Solid phase peptide synthesis procedures are well known in the art and further described by John Morrow Stewart and Janis Dillaha Young, Solid Phase Peptide Syntheses (2nd Ed., Pierce Chemical Company, 1984).

Both the cyclic and the linear polymers presented herein can be purified, for example, by preparative high performance liquid chromatography [Creighton T. (1983) Proteins, structures and molecular principles. WH Freeman and Co. N.Y.].

Apart from having beneficial antimicrobial activity per se, as detailed herein, either the cyclic or the linear polymers of the present invention may include an additional active agent attached thereto.

As used herein, the phrase "active agent" refers to a compound or a portion of a compound, which exhibits a pharmacological or biological beneficial activity per se. Examples include a therapeutically active agent, a targeting agent, a labeling agent (such as for imaging and diagnostic purposes) and the likes. According to embodiments of the present invention, a polymer can have more than one active agents attached thereto, and more than one type of active agents attached thereto.

The conjugation of the additional active agent to a polymer presented herein can provide a dual utility for the polymer. When the additional active agent is a labeling agent, the conjugation thereof to an antimicrobial polymer of the present invention, having a high affinity to microbial cells, can assist in the location, diagnosis and targeting of microbial growth loci in a host. When the additional active agent is a therapeutically active agent, the conjugation thereof to an antimicrobial polymer of the present invention will exert a dual and possibly synergistic antimicrobial activity.

According to preferred embodiments of the present invention, the one or more active agents may be attached to either the cyclic or the linear polymer at any substitutable position. Examples of such substitutable positions include, without limitation, a side chain of any one or more of the amino acid residues in either the cyclic or the linear polymer, any one of the linking moieties of either the cyclic or the linear polymer, any one of the N- and C-termini of the linear polymer and any one or more of the hydrophobic moiety residues in either the cyclic or the linear polymer.

Hence, as used herein, the phrase "a therapeutically active agent" describes a chemical substance, which exhibits a therapeutic activity when administered to a subject As used herein, the term "targeting agent" describes agents which have a specific affinity to specific cells or tissues. Targeting agents may be used to deliver any antimicrobial agent in general and an antimicrobial polymer according to the present embodiments in particular, to specific cells and tissues. The result is an enhanced effect and an improved exposure of the infected cells and/or tissues to the antimicrobial polymer, preferably accompanied by reduced exposure of non-infected cells thereto. Targeting agents include, for example, porphyrins, hormones, peptides, proteins, receptor ligands, antigens, haptens, antibodies and fragments thereof As used herein, the phrase "labeling agent" refers to a detectable moiety or a probe and includes, for example, chromophores, fluorescent compounds, phosphorescent compounds, heavy metal clusters, and radioactive labeling compounds, as well as any other known detectable moieties.

Labeling of microbial growth loci in a host is critical for the diagnosis and efficient targeting of the photogenic microorganism and treatment thereof.

Adding a therapeutically active agent to either the cyclic or the linear polymer can provide a solution for many deficiencies of presently known therapeutically active agent against photogenic microorganisms, such as resistance of the photogenic microorganism to the therapeutically active agent, specificity of the therapeutically active agent to photogenic microorganism and general efficacy weakness. Both the cyclic and the linear polymers of the present invention can exhibit not only antimicrobial activity per se by virtue of their structure and chemical properties, but can also provide targeting capacity as a delivery vehicle to a presently know therapeutically active agents and further provide membrane permeability to presently know therapeutically active agents due to their capability to exert disturbance in the membrane structure of photogenic microorganisms.

Non-limiting examples of therapeutically active agents that can be beneficially used in this and other contexts of the present invention include, without limitation, one or more of an agonist residue, an amino acid residue, an analgesic residue, an antagonist residue, an antibiotic agent residue, an antibody residue, an antidepressant agent, an antigen residue, an anti-histamine residue, an anti-hypertensive agent, an anti-inflammatory drug residue, an anti-metabolic agent residue, an antimicrobial agent residue, an antioxidant residue, an anti-proliferative drug residue, an antisense residue, a chemotherapeutic drug residue, a co-factor residue, a cytokine residue, a drug residue, an enzyme residue, a growth factor residue, a heparin residue, a hormone residue, an immunoglobulin residue, an inhibitor residue, a ligand residue, a nucleic acid residue, an oligonucleotide residue, a peptide residue, a phospholipid residue, a prostaglandin residue, a protein residue, a toxin residue, a vitamin residue and any combination thereof The combined therapeutic effect is particularly advantageous when the therapeutically active agent is an antimicrobial or an antibiotic agent. The combined activity of either the cyclic or the linear polymers of the present invention and that of an additional antimicrobial/antibiotic agent may provide the antimicrobial/antibiotic agent the capacity to overcome the known limitations of these drugs such as targeting, specificity, efficacy, drug-resistance etcetera. Synergism may also be achieved.

Non-limiting examples of antimicrobial and antibiotic agents that are suitable for use in this context of the present invention include, without limitation, mandelic acid, 2,4-dichlorobenzenemethanol, 4-[bis(ethylthio)methyl]-2-methoxyphenol, 4-epi-tetracycline, 4-hexylresorcinol, 5,12-dihydro-5,7,12,14-tetrazapentacen, 5-chlorocarvacrol, 8-hydroxyquinoline, acetarsol, acetylkitasamycin, acriflavin, alatrofloxacin, ambazon, amfomycin, amikacin, amikacin sulfate, aminoacridine, aminosalicylate calcium, aminosalicylate sodium, aminosalicylic acid, ammoniumsulfobituminat, amorolfin, amoxicillin, amoxicillin sodium, amoxicillin trihydrate, amoxicillin-potassium clavulanate combination, amphotericin B, ampicillin, ampicillin sodium, ampicillin trihydrate, ampicillin-sulbactam, apalcillin, arbekacin, aspoxicillin, astromicin, astromicin sulfate, azanidazole, azidamfenicol, azidocillin, azithromycin, azlocillin, aztreonam, bacampicillin, bacitracin, bacitracin zinc, bekanamycin, benzalkonium, benzethonium chloride, benzoxonium chloride, berberine hydrochloride, biapenem, bibrocathol, biclotymol, bifonazole, bismuth subsalicylate, bleomycin antibiotic complex, bleomycin hydrochloride, bleomycin sulfate, brodimoprim, bromochlorosalicylanilide, bronopol, broxyquinolin, butenafine, butenafine hydrochloride, butoconazol, calcium undecylenate, candicidin antibiotic complex, capreomycin, carbenicillin, carbenicillin disodium, carfecillin, carindacillin, carumonam, carzinophilin, caspofungin acetate, cefacetril, cefaclor, cefadroxil, cefalexin, cefalexin hydrochloride, cefalexin sodium, cefaloglycin, cefaloridine, cefalotin, cefalotin sodium, cefamandole, cefamandole nafate, cefamandole sodium, cefapirin, cefapirin sodium, cefatrizine, cefatrizine propylene glycol, cefazedone, cefazedone sodium salt, cefazolin, cefazolin sodium, cefbuperazone, cefbuperazone sodium, cefcapene, cefcapene pivoxil hydrochloride, cefdinir, cefditoren, cefditoren pivoxil, cefepime, cefepime hydrochloride, cefetamet, cefetamet pivoxil, cefixime, cefmenoxime, cefmetazole, cefmetazole sodium, cefminox, cefminox sodium, cefmolexin, cefodizime, cefodizime sodium, cefonicid, cefonicid sodium, cefoperazone, cefoperazone sodium, ceforanide, cefoselis sulfate, cefotaxime, cefotaxime sodium, cefotetan, cefotetan disodium, cefotiam, cefotiam hexetil hydrochloride, cefotiam hydrochloride, cefoxitin, cefoxitin sodium, cefozopran hydrochloride, cefpiramide, cefpiramide sodium, cefpirome, cefpirome sulfate, cefpodoxime, cefpodoxime proxetil, cefprozil, cefquinome, cefradine, cefroxadine, cefsulodin, ceftazidime, cefteram, cefteram pivoxil, ceftezole, ceftibuten, ceftizoxime, ceftizoxime sodium, ceftriaxone, ceftriaxone sodium, cefuroxime, cefuroxime axetil, cefuroxime sodium, cetalkonium chloride, cetrimide, cetrimonium, cetylpyridinium, chloramine T, chloramphenicol, chloramphenicol palmitate, chloramphenicol succinate sodium, chlorhexidine, chlormidazole, chlormidazole hydrochloride, chloroxylenol, chlorphenesin, chlorquinaldol, chlortetracycline, chlortetracycline hydrochloride, ciclacillin, ciclopirox, cinoxacin, ciprofloxacin, ciprofloxacin hydrochloride, citric acid, clarithromycin, clavulanate potassium, clavulanate sodium, clavulanic acid, clindamycin, clindamycin hydrochloride, clindamycin palmitate hydrochloride, clindamycin phosphate, clioquinol, cloconazole, cloconazole monohydrochloride, clofazimine, clofoctol, clometocillin, clomocycline, clotrimazol, cloxacillin, cloxacillin sodium, colistin, colistin sodium methanesulfonate, colistin sulfate, cycloserine, dactinomycin, danofloxacin, dapsone, daptomycin, daunorubicin, DDT, demeclocycline, demeclocycline hydrochloride, dequalinium, dibekacin, dibekacin sulfate, dibromopropamidine, dichlorophene, dicloxacillin, dicloxacillin sodium, didecyldimethylammonium chloride, dihydrostreptomycin, dihydrostreptomycin sulfate, diiodohydroxyquinolin, dimetridazole, dipyrithione, dirithromycin, DL-menthol, D-menthol, dodecyltriphenylphosphonium bromide, doxorubicin, doxorubicin hydrochloride, doxycycline, doxycycline hydrochloride, econazole, econazole nitrate, enilconazole, enoxacin, enrofloxacin, eosine, epicillin, ertapenem sodium, erythromycin, erythromycin estolate, erythromycin ethyl succinate, erythromycin lactobionate, erythromycin stearate, ethacridine, ethacridine lactate, ethambutol, ethanoic acid, ethionamide, ethyl alcohol, eugenol, exalamide, faropenem, fenticonazole, fenticonazole nitrate, fezatione, fleroxacin, flomoxef, flomoxef sodium, florfenicol, flucloxacillin, flucloxacillin magnesium, flucloxacillin sodium, fluconazole, flucytosine, flumequine, flurithromycin, flutrimazole, fosfomycin, fosfomycin calcium, fosfomycin sodium, framycetin, framycetin sulphate, furagin, furazolidone, fusafungin, fusidic acid, fusidic acid sodium salt, gatifloxacin, gemifloxacin, gentamicin antibiotic complex, gentamicin c1a, gentamycin sulfate, glutaraldehyde, gramicidin, grepafloxacin, griseofulvin, halazon, haloprogine, hetacillin, hetacillin potassium, hexachlorophene, hexamidine, hexetidine, hydrargaphene, hydroquinone, hygromycin, imipenem, isepamicin, isepamicin sulfate, isoconazole, isoconazole nitrate, isoniazid, isopropanol, itraconazole, josamycin, josamycin propionate, kanamycin, kanamycin sulphate, ketoconazole, kitasamycin, lactic acid, lanoconazole, lenampicillin, leucomycin A1, leucomycin A13, leucomycin A4, leucomycin A5, leucomycin A6, leucomycin A7, leucomycin A8, leucomycin A9, levofloxacin, lincomycin, lincomycin hydrochloride, linezolid, liranaftate, 1-menthol, lomefloxacin, lomefloxacin hydrochloride, loracarbef, lymecyclin, lysozyme, mafenide acetate, magnesium monoperoxophthalate hexahydrate, mecetronium ethylsulfate, mecillinam, meclocycline, meclocycline sulfosalicylate, mepartricin, merbromin, meropenem, metalkonium chloride, metampicillin, methacycline, methenamin, methyl salicylate, methylbenzethonium chloride, methylrosanilinium chloride, meticillin, meticillin sodium, metronidazole, metronidazole benzoate, mezlocillin, mezlocillin sodium, miconazole, miconazole nitrate, micronomicin, micronomicin sulfate, midecamycin, minocycline, minocycline hydrochloride, miocamycin, miristalkonium chloride, mitomycin c, monensin, monensin sodium, morinamide, moxalactam, moxalactam disodium, moxifloxacin, mupirocin, mupirocin calcium, nadifloxacin, nafcillin, nafcillin sodium, naftifine, nalidixic acid, natamycin, neomycin a, neomycin antibiotic complex, neomycin C, neomycin sulfate, neticonazole, netilmicin, netilmicin sulfate, nifuratel, nifuroxazide, nifurtoinol, nifurzide, nimorazole, niridazole, nitrofurantoin, nitrofurazone, nitroxolin, norfloxacin, novobiocin, nystatin antibiotic complex, octenidine, ofloxacin, oleandomycin, omoconazol, orbifloxacin, ornidazole, ortho-phenylphenol, oxacillin, oxacillin sodium, oxiconazole, oxiconazole nitrate, oxoferin, oxolinic acid, oxychlorosene, oxytetracycline, oxytetracycline calcium, oxytetracycline hydrochloride, panipenem, paromomycin, paromomycin sulfate, pazufloxacine, pefloxacin, pefloxacin mesylate, penamecillin, penicillin G, penicillin G potassium, penicillin G sodium, penicillin V, penicillin V calcium, penicillin V potassium, pentamidine, pentamidine diisetionate, pentamidine mesilas, pentamycin, phenethicillin, phenol, phenoxyethanol, phenylmercuriborat, PHMB, phthalylsulfathiazole, picloxydin, pipemidic acid, piperacillin, piperacillin sodium, pipercillin sodium-tazobactam sodium, piromidic acid, pivampicillin, pivcefalexin, pivmecillinam, pivmecillinam hydrochloride, policresulen, polymyxin antibiotic complex, polymyxin B, polymyxin B sulfate, polymyxin B1, polynoxylin, povidone-iodine, propamidin, propenidazole, propicillin, propicillin potassium, propionic acid, prothionamide, protiofate, pyrazinamide, pyrimethamine, pyrithion, pyrrolnitrin, quinoline, quinupristin-dalfopristin, resorcinol, ribostamycin, ribostamycin sulfate, rifabutin, rifampicin, rifamycin, rifapentine, rifaximin, ritiometan, rokitamycin, rolitetracycline, rosoxacin, roxithromycin, rufloxacin, salicylic acid, secnidazol, selenium disulphide, sertaconazole, sertaconazole nitrate, siccanin, sisomicin, sisomicin sulfate, sodium thiosulfate, sparfloxacin, spectinomycin, spectinomycin hydrochloride, spiramycin antibiotic complex, spiramycin b, streptomycin, streptomycin sulphate, succinylsulfathiazole, sulbactam, sulbactam sodium, sulbenicillin disodium, sulbentin, sulconazole, sulconazole nitrate, sulfabenzamide, sulfacarbamide, sulfacetamide, sulfacetamide sodium, sulfachlorpyridazine, sulfadiazine, sulfadiazine silver, sulfadiazine sodium, sulfadicramide, sulfadimethoxine, sulfadoxine, sulfaguanidine, sulfalene, sulfamazone, sulfamerazine, sulfamethazine, sulfamethazine sodium, sulfamethizole, sulfamethoxazole, sulfamethoxazol-trimethoprim, sulfamethoxypyridazine, sulfamonomethoxine, sulfamoxol, sulfanilamide, sulfaperine, sulfaphenazol, sulfapyridine, sulfaquinoxaline, sulfasuccinamide, sulfathiazole, sulfathiourea, sulfatolamide, sulfatriazin, sulfisomidine, sulfisoxazole, sulfisoxazole acetyl, sulfonamides, sultamicillin, sultamicillin tosilate, tacrolimus, talampicillin hydrochloride, teicoplanin A2 complex, teicoplanin A2-1, teicoplanin A2-2, teicoplanin A2-3, teicoplanin A2-4, teicoplanin A2-5, teicoplanin A3, teicoplanin antibiotic complex, telithromycin, temafloxacin, temocillin, tenoic acid, terbinafine, terconazole, terizidone, tetracycline, tetracycline hydrochloride, tetracycline metaphosphate, tetramethylthiuram monosulfide, tetroxoprim, thiabendazole, thiamphenicol, thiaphenicol glycinate hydrochloride, thiomersal, thiram, thymol, tibezonium iodide, ticarcillin, ticarcillin-clavulanic acid mixture, ticarcillin disodium, ticarcillin monosodium, tilbroquinol, tilmicosin, tinidazole, tioconazole, tobramycin, tobramycin sulfate, tolciclate, tolindate, tolnaftate, toloconium metilsulfat, toltrazuril, tosufloxacin, triclocarban, triclosan, trimethoprim, trimethoprim sulfate, triphenylstibinsulfide, troleandomycin, trovafloxacin, tylosin, tyrothricin, undecoylium chloride, undecylenic acid, vancomycin, vancomycin hydrochloride, viomycin, virginiamycin antibiotic complex, voriconazol, xantocillin, xibornol and zinc undecylenate.

Major parts of either the cyclic or the linear polymers of the present embodiments are based on a repetitive element consisting of a conjugate between an amino acid and a bi-functional hydrophobic moiety. The conjugate may repeat several times in the sequence of the polymer and/or be interrupted and/or flanked by a difference types of conjugates or by single or repeats of amino acid residues and single or repeats of hydrophobic moiety residues.

Hence, according to another aspect of the present invention, there is provided a conjugate which includes an amino acid residue and a hydrophobic moiety residue, as defined and described hereinabove, attached to a functional group on the side-chain of the amino acid residue. The hydrophobic moiety residue in the conjugate according to preferred embodiments is designed such that is it capable of forming a bond with an N-alpha or a C-alpha of an additional amino acid residue. Preferably, the hydrophobic moiety residue is conjugated to the side-chain of the amino acid residue via a peptide bond.

The hydrophobic moiety of the conjugate of the present invention is having a bi-functional design which allows the conjugate to serve as a polymerizable conjugate that can form a part of the polymers described and presented herein. Preferably, the hydrophobic moiety which forms a part of the conjugate is having a bi-functionality in the form of a carboxylic group at one end thereof and an amine group at the other end thereof.

Hence, according to another aspect of the present invention, there is provided a process of preparing the conjugate described hereinabove, the general process is based on providing an amino acid, preferably the amino acid is a positively charged amino acid which comprises a functional group in its side-chain, such as histidine, lysine, ornithine and arginine; providing a hydrophobic moiety as defined and discussed hereinabove having at least two functional groups that are capable of reacting with a functional group in the side-chain of the amino acid, or the N-alpha thereof the C-alpha thereof and linking one of the functional groups in the hydrophobic moiety to the functional group in the side-chain of the amino acid.

Preferably, the link between the side-chain of the amino acid and the hydrophobic moiety is via a peptide bond.

In order to form a peptide bond linking the amino acid to the hydrophobic moiety, the hydrophobic moiety preferably has a carboxylic group at one end thereof and an amine group at the other end thereof.

Either the cyclic or the linear antimicrobial polymers as described herein can be beneficially utilized in the treatment of pathogenic microorganism infections, as these are defined hereinbelow. As demonstrated in the Example section that follows, such polymers are by themselves capable of exerting antimicrobial activity. The option to include an additional therapeutically active agent may thus act synergistically as toxic agents against various bacteria, fungi and other microorganisms.

Herein throughout, the phrase "pathogenic microorganism" is used to describe any microorganism which can cause a disease or disorder in a higher organism, such as mammals in general and a human in particular. The pathogenic microorganism may belong to any family of organisms such as, but not limited to prokaryotic organisms, eubacterium, archaebacterium, eukaryotic organisms, yeast, fungi, algae, protozoan, and other parasites. Non-limiting examples of pathogenic microorganism are *Plasmodium falciparum* and related malaria-causing protozoan parasites, *Acanthamoeba* and other free-living amoebae, *Aeromonas hydrophile, Anisakis* and related worms, *Acinetobacter baumanii, Ascaris lumbricoides, Bacillus cereus, Brevundimonas diminuta, Campylobacter jejuni, Clostridium botulinum, Clostridium perfringens, Cryptosporidium parvum, Cyclospora cayetanensis, Diphyllobothrium, Entamoeba histolytica*, certain strains of *Escherichia coli, Eustrongylides, Giardia lamblia, Klebsiella pneumoniae, Listeria monocytogenes, Nanophyetus, Plesiomonas shigelloides, Proteus mirabilis, Pseudomonas aeruginosa, Salmonella, Serratia odorifera, Shigella, Staphylococcus aureus, Stenotrophomonas maltophilia, Streptococcus, Trichuris trichiura, Vibrio cholerae, Vibrio parahaemolyticus, Vibrio vulnificus* and other vibrios, *Yersinia enterocolitica, Yersinia pseudotuberculosis* and *Yersinia kristensenii*.

Hence, according to another aspect of the present invention, there is provided a method of treating a medical condition associated with a pathogenic microorganism, the method includes administering to a subject in need thereof a therapeutically effective amount of one or more of the cyclic or the linear polymers, as described hereinabove As used herein, the terms "treating" and "treatment" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "therapeutically effective amount" describes an amount of the composite being administered which will relieve to some extent one or more of the symptoms of the condition being treated.

The method of treatment, according to an embodiment of the present invention, may include the administration of an additional therapeutically active agent, as this is defined and discussed hereinabove.

As mentioned above and demonstrated in the Example section that follows, both the cyclic and the linear antimicrobial polymers of the present invention, alone or in combination with any other therapeutically active agents, can be designed and utilized to destroy pathological microorganisms. The destruction of a pathogenic microorganism is effected by selectively destructing a portion of the cells of a pathogenic microorganism. While most known antibiotics act by interfering selectively with the biosynthesis of one or more of the molecular constituents of the cell-membrane, proteins or nucleic acids, both the cyclic and the linear polymers of the present invention also act by binding and disrupting the outer membrane of the pathogenic microorganism cells. Disrupting the outer membrane of a cell causes its death due to membrane depolarization, leakage of metabolites and/or total loss of cell integrity; therefore the polymers of the present invention also act directly as effective antimicrobial agents by disrupting the metabolism and/or the multiplication processes of the pathogenic microorganism.

As mentioned above and demonstrated in the Example section that follows, the polymers presented herein may act as antimicrobial agents which do not evoke the appearance of resistance thereto. The possible development of resistance to the either the cyclic or the linear polymers of the present invention was tested by measuring the minimal inhibitory concentration (MIC) levels following multiple exposures of the bacteria to exemplary polymers according to the present invention. The results obtained in the antimicrobial-resistance studies in bacteria presented hereinbelow, showed that exposing bacteria, and even strains that already developed resistance to classical antibiotics, to the antimicrobial polymers presented herein did not result in development of resistance.

As is further mentioned above and demonstrated in the Example section that follows, both the cyclic and the linear polymers presented herein are non-toxic to mammals.

Medical conditions associated with a pathogenic microorganism include infections, infestation, contaminations and transmissions by or of pathogenic microorganism. In general, a disease causing infection is the invasion into the tissues of a plant or an animal by pathogenic microorganisms. The invasion of body tissues by parasitic worms and other higher pathogenic organisms is commonly referred to as infestation.

Invading organisms such as bacteria produce toxins that damage host tissues and interfere with normal metabolism; some toxins are actually enzymes that break down host tissues. Other bacterial substances may inflict their damage by destroying the host's phagocytes, rendering the body more susceptible to infections by other pathogenic microorganisms. Substances produced by many invading organisms cause allergic sensitivity in the host. Infections may be spread via respiratory droplets, direct contact, contaminated food, or vectors, such as insects. They can also be transmitted sexually and from mother to fetus.

Diseases caused by bacterial infections typically include, for example, actinomycosis, anthrax, aspergillosis, bacteremia, bacterial skin diseases, *bartonella* infections, botulism, brucellosis, *burkholderia* infections, *campylobacter* infections, candidiasis, cat-scratch disease, chlamydia infections, cholera, *clostridium* infections, coccidioidomycosis, cryptococcosis, dermatomycoses, diphtheria, ehrlichiosis, epidemic louse borne typhus, *Escherichia coli* infections, fusobacterium infections, gangrene, general infections, general mycoses, gonorrhea, gram-negative bacterial infections, gram-positive bacterial infections, histoplasmosis, impetigo, *klebsiella* infections, legionellosis, leprosy, leptospirosis, listeria infections, lyme disease, malaria, maduromycosis, melioidosis, *mycobacterium* infections, *mycoplasma* infections, necrotizing fasciitis, nocardia infections, onychomycosis, ornithosis, pneumococcal infections, pneumonia, *pseudomonas* infections, Q fever, rat-bite fever, relapsing fever, rheumatic fever, rickettsia infections, Rocky-mountain spotted fever, salmonella infections, scarlet fever, scrub typhus, sepsis, sexually transmitted bacterial diseases, staphylococcal infections, streptococcal infections, surgical site infection, tetanus, tick-borne diseases, tuberculosis, tularemia, typhoid fever, urinary tract infection, *vibrio* infections, yaws, *yersinia* infections, *Yersinia pestis* plague, zoonoses and zygomycosis.

Both the cyclic and the linear polymers of the present embodiments can therefore be used to treat medical conditions caused by pathogenic microorganisms by virtue of their anti-microbial effects inflicted upon the pathogenic microorganisms by one of the abovementioned mechanism which mostly stem from their specific and selective affinity to the membrane of the pathogenic microorganism, and relative undamaging effect they have on mammalian cell. This affinity can be used to weaken, disrupt, puncture, melt, fuse and/or mark the membrane of a pathogenic microorganism.

The pathogenic microorganism may be destroyed directly by the disruption of its membrane as demonstrated and presented for a series of bacterial strains in the Examples section that follows, or be weakened so as to allow the innate immune system to destroy it or slow down its metabolism and therefore its reproduction so as to allow the innate immune system to overcome the infection.

The pathogenic microorganism may be destroyed by the disruption of its membrane so as to allow a therapeutically active agent, such as an antibiotic agent, to more easily penetrate the cell of the microorganism and afflict its activity thereon.

The latter capacity of the antimicrobial polymer of the present invention to assist the penetration of another therapeutically active agent into the cells of the pathogenic microorganism can be utilized to treat many infectious diseases, such as, for example, malaria.

The experimental results presented in the Examples section that follows suggests that secondary structure might not be an absolute prerequisite for antimicrobial properties. On another hand, evident from these results stems that the only property which is shared by all typical AMPs, and also shared by the polymers of the present invention, is the relative abundance of both hydrophobic and positively charged amino acid residues. Thus, according to the present invention, the antimicrobial polymers presented are endowed with varied positive charge and hydrophobicity and substantially lack secondary structure.

In any of the aspects of the present invention, either the cyclic or the linear antimicrobial polymers of the present invention can be utilized either per se, or as an active ingredient that forms a part of a pharmaceutical composition, with or without an additional therapeutically active agent, and a pharmaceutically acceptable carrier.

Hence, according to still another aspect of the present invention, there are provided pharmaceutical compositions, which comprise one or more of either the cyclic or the linear polymers of the present invention as described above having an antimicrobial activity and a pharmaceutically acceptable carrier.

As used herein a "pharmaceutical composition" refers to a preparation of the antimicrobial polymer described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the silver-coated enzymes into preparations which, can be used pharmaceutically. Proper formulation is dependent upon the route of administration chosen. Toxicity and therapeutic efficacy of the silver-coated enzymes described herein can be determined by standard pharmaceutical procedures in experimental animals, e.g., by determining the $EC_{50}$, the $IC_{50}$ and the $LD_{50}$ (lethal dose causing death in 50% of the tested animals) for a subject silver-coated enzyme. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a silver-coated enzyme of the invention formulated in a compatible pharmaceutical carrier may also be prepared, placed in an appropriate container, and labeled for treatment of an indicated condition or diagnosis, as is detailed hereinabove.

Thus, according to an embodiment of the present invention, depending on the selected polymers and the presence of additional active ingredients, the pharmaceutical composition according to preferred embodiments, is packaged in a packaging material and identified in print, in or on the packaging material, for use in the treatment of a medical condition associated with a pathogenic microorganism, as is defined hereinabove and a parasite.

The pharmaceutical composition comprising either a cyclic or a linear polymer of the present embodiments may further comprise at least one additional therapeutically active agent, as this is defined and presented hereinabove.

The polymers of the present embodiments can be further beneficially utilized as active substances in various medical devices.

Hence, according to an additional aspect of the present invention there is provided a medical device which includes one or more of either the cyclic or the linear polymers of the present embodiments, described hereinabove, and a delivery system configured for delivering the polymer(s) to a bodily site of a subject.

The medical devices according to the present invention are therefore used for delivering to or applying on a desired bodily site either the cyclic or the linear polymers of the present invention. The polymers can be incorporated in the medical devices either per se or as a part of a pharmaceutical composition, as described hereinabove.

As used herein, the phrase "bodily site" includes any organ, tissue, membrane, cavity, blood vessel, tract, biological surface or muscle, which delivering thereto or applying thereon the polymers of the present invention is beneficial.

Exemplary bodily sites include, but are not limited to, the skin, a dermal layer, the scalp, an eye, an ear, a mouth, a throat, a stomach, a small intestines tissue, a large intestines tissue, a kidney, a pancreas, a liver, the digestive system, the respiratory tract, a bone marrow tissue, a mucosal membrane, a nasal membrane, the blood system, a blood vessel, a muscle, a pulmonary cavity, an artery, a vein, a capillary, a heart, a heart cavity, a male or female reproductive organ and any visceral organ or cavity.

The medical devices according to this aspect of the present invention can be any medical device known in the art, including those defined and classified, for example, by the FDA and specified in www.fda.gov/cdrh/devadvice/313.html (e.g., Class I, II and III), depending e.g., on the condition and bodily site being treated.

Thus, for example, in one embodiment of this aspect of the present invention, the medical device comprises a delivery system that is configured to deliver either the cyclic or the linear polymer(s) by inhalation. Such inhalation devices are useful for delivering the polymers of the present invention to, e.g., the respiratory tract.

The delivery system in such medical devices may be based on any of various suitable types of respiratory delivery systems which are suitable for administering a therapeutically effective dose of the polymer(s) of the present invention to a subject. The inhalation device may be configured to deliver to the respiratory tract of the subject, preferably via the oral and/or nasal route, the compound in the form of an aerosol/spray, a vapor and/or a dry powder mist. Numerous respiratory systems and methods of incorporating therapeutic agents therein, such as the polymers of the present invention, suitable for assembly of a suitable inhalation device are widely employed by the ordinarily skilled artisan and are extensively described in the literature of the art (see, for example to U.S. Pat. Nos. 6,566,324, 6,571,790, 6,637,430, and 6,652,323; U.S. Food & Drug Administration (USFDA) Center For Drug Evaluation and Research (CDER); www.mece.ualberta.ca/arla/tutorial.htm).

The respiratory delivery system may thus be, for example, an atomizer or aerosol generator such as a nebulizer inhaler, a dry powder inhaler (DPI) and a metered dose inhaler (MDI), an evaporator such as an electric warmer and a vaporizer, and a respirator such as a breathing machine, a body respirator (e.g., cuirass), a lung ventilator and a resuscitator.

In still another embodiment of this aspect of the present invention, the medical device is such that delivering either the cyclic or the linear polymer(s) is effected transdermally. In this embodiment, the medical device is applied on the skin of a subject, so as to transdermally deliver the polymer(s) to the blood system.

Exemplary medical devices for transdermally delivering a polymer according to the present invention include, without limitation, an adhesive plaster and a skin patch. Medical devices for transdermal or transcutaneous delivery of the polymer(s) typically further include one or more penetration enhancers, for facilitating their penetration through the epidermis and into the system.

According to another embodiment of this aspect of the present invention, the medical device is such that delivering either the cyclic or the linear polymer(s) is effected by topically applying the medical device on a biological surface of a subject. The biological surface can be, for example, a skin, scalp, an eye, an ear and a nail. Such medical devices can be used in the treatment of various skin conditions and injuries, eye and ear infections and the like.

Exemplary medical devices for topical application include, without limitation, an adhesive strip, a bandage, an adhesive plaster, a wound dressing and a skin patch.

In another embodiment of this aspect of the present invention, the medical device is such that delivering either the cyclic or the linear polymer(s) is effected by implanting the medical device in a bodily organ. As used herein, the term "organ" further encompasses a bodily cavity.

The organ can be, for example, a pulmonary cavity, a heart or heart cavity, a bodily cavity, an organ cavity, a blood vessel, an artery, a vein, a muscle, a bone, a kidney, a capillary, the space between dermal layers, an organ of the female or male reproductive system, an organ of the digestive tract and any other visceral organ.

The medical device according to this embodiment of the present invention typically includes a device structure in which either a cyclic or a linear polymer according to the present invention is incorporated. The polymer(s) can thus be, for example, applied on, entrapped in or attached to (chemically, electrostatically or otherwise) the device structure.

The device structure can be, for example, metallic structure and thus may be comprised of a biocompatible metal or mixture of metals (e.g., gold, platinum).

Alternatively, the device structure may be comprised of other biocompatible matrices. These can include, for example, plastics, silicon, polymers, resins, and may include at least one component such as, for example, polyurethane, cellulose ester, polyethylene glycol, polyvinyl acetate, dextran, gelatin, collagen, elastin, laminin, fibronectin, vitronectin, heparin, segmented polyurethane-urea/heparin, poly-L-lactic acid, fibrin, cellulose and amorphous or structured carbon such as in fullerenes, and any combination thereof In cases where a biodegradable implantable device is desired, the device structure can be comprised of a biocompatible matrix that is biodegradable. Biodegradable matrices can include, for example, biodegradable polymers such as poly-L-lactic acid.

Optionally, the device structure may be comprised of biocompatible metal(s) coated with other biocompatible matrix.

Further optionally, in cases where a device which releases either the cyclic or the linear polymer(s) of the present invention in a controlled manner is desired, the device structure can be comprised of or coated with a biocompatible matrix that functions as or comprises a slow release carrier. The biocompatible matrix can therefore be a slow release carrier which is dissolved, melted or liquefied upon implantation in the desired site or organ. Alternatively, the biocompatible matrix can be a pre-determined porous material which entraps the polymer(s) in the pores. When implanted in a desired site, the polymer(s) diffuse out of the pores, whereby the diffusion rate is determined by the pores size and chemical nature. Further alternatively, the biocompatible matrix can comprise a biodegradable matrix, which upon degradation releases the polymer(s) of the present invention.

Both the cyclic and the linear polymer(s) of the present invention can be incorporated in the device structure by any methodology known in the art, depending on the selected nature of the device structure. For example, either the cyclic or the linear polymer(s) can be entrapped within a porous matrix, swelled or soaked within a matrix, or being adhered to a matrix.

Much like their antimicrobial activity in the body, the antimicrobial activity of both the cyclic and the linear polymers of the present invention may further be harnessed for the preservation of food ingredients and products.

Hence, according to yet another aspect of the present invention there is provided a food preservative comprising an effective amount of either the cyclic or the linear polymer of the present invention as described herein.

The polymer(s) may be incorporated into the food product as one of its ingredients either per se, or with an edible carrier.

Both the cyclic and the linear polymers of the present invention have high and selective affinity towards membranes of microorganisms. This attribute is one of the main elements which contribute to the beneficial and efficacious activity of the polymers when utilized as an antimicrobial agent. When either the cyclic or the linear polymer is coupled with a labeling agent, this membrane binding attribute can be further employed to label colonies and proliferation sites of microorganisms, especially microbial growth loci in a host in vivo.

Hence, according to another aspect of the present invention there is provided an imaging probe for detecting a pathogenic microorganism, the imaging probe comprising either a cyclic or a linear polymer as defined and described hereinabove, whereas the polymer further includes at least one labeling agent, as defined hereinabove, attached thereto. When released to the environment, these polymers, having a labeling agent attached thereto will bind to the membrane of cell of microorganisms and therefore attach the labeling agent to the cells of the microorganism.

As used herein, the term "chromophore" refers to a chemical moiety that, when attached to another molecule, renders the latter colored and thus visible when various spectrophotometric measurements are applied.

The phrase "fluorescent compound" refers to a compound that emits light at a specific wavelength during exposure to radiation from an external source.

The phrase "phosphorescent compound" refers to a compound emitting light without appreciable heat or external excitation as by slow oxidation of phosphorous.

A heavy metal cluster can be for example a cluster of gold atoms used, for example, for labeling in electron microscopy techniques.

According to preferred embodiments of the present invention, one or more labeling agents may be attached to the polymer at any substitutable position, as in the case of an active agent discussed above. Examples of such substitutable positions are, without limitation, a side chain of any one or more of the amino acid residues in the polymer, any one of the linking moieties of the polymer, any one of the N- and C-termini of the polymer and any one or more of the hydrophobic moiety residues in the polymer.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions; illustrate the invention in a non limiting fashion.

Materials and Experimental Methods

Chemical Syntheses:
Materials:
Lysine having Fmoc ((9H-fluoren-9-yl)methyl carbonate) protection on its main-chain (alpha-) amine group and Boc (tent-butyl carbonate) protection on its side-chain amine group was purchased from Applied Biosystems and from NovaBiochem.

ω-amino fatty acids such as 4-amino-butyric acid, 8-amino-caprylic acid and 12-amino-lauric acid having Fmoc protection of the amine group were purchased from Sigma-Aldrich/NovaBiochem.

All other solvents and reagents used were purchased from Sigma-Aldrich/NovaBiochem/Applied Biosystems/J. T. Baker and were used without further purification.

Preparation of Libraries of Antimicrobial Polymers—General Procedure:

The polymers according to the present invention were prepared by a solid phase method and were purified to chromatographic homogeneity according to methodologies described in the art (Feder, R. et al. (2000) *J. Biol. Chem.* 275, 4230-4238). Briefly, the polymers were synthesized by applying the Fmoc active ester chemistry on a fully automated, programmable peptide synthesizer (Applied Biosystems 433A). After cleavage from the resin, the crude polymers were extracted with 30% acetonitrile in water and purified to obtain a chromatographic homogeneity greater than 95%, as determined by HPLC (Alliance Waters).

HPLC chromatograms were performed on C18 columns (Vydak, 250 mm×4.6 or 10 mm) using a linear gradient of acetonitrile in water (1% per minute), both solvents contained 0.1% trifluoroacetic acid. The purified polymers were subjected to mass spectrometry (ZQ Waters) to confirm their composition and stored as a lyophilized powder at −20° C. Prior to being tested, fresh solutions were prepared in water, mixed by vortex, solubilized by ultrasound, centrifuged and then diluted in the appropriate medium.

In order to estimate the hydrophobicity of each polymer, the polymer was eluted with a linear gradient of acetonitrile (1% per minute) on an HPLC reversed-phase C18 column, and the percent of acetonitrile at which the polymer was eluted was used for hydrophobicity estimation (see, "ACN (%)" in Table 3 below).

Exemplary building units which were utilized in the synthesis described above are presented in Scheme 1 below and include: lysine and an ω-amino-fatty acid having m carbon atoms (Compound I).

Synthesis of exemplary polymers according to the present invention, which are comprised of lysine and Compound I, was performed by adding an Fmoc/Boc-protected lysine and an Fmoc-protected Compound I separately and sequentially to the resin according to conventional peptide solid phase synthesis protocols.

Scheme 1

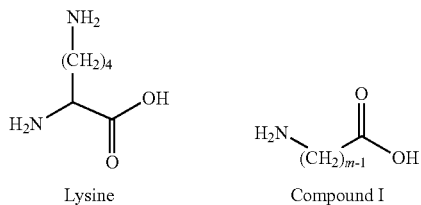

Lysine      Compound I

In Vitro Studies:
Bacterial Strains and Sample Preparation:
Antibacterial activity was determined using the following strains, cultured in LB medium (10 grams/liter trypton, 5 grams/liter yeast extract, 5 grams/liter NaCl, pH 7.4): *Escherichia coli* (ATCC (American Type Culture Collection)

35218); methicillin resistant *Staphylococcus aureus* (CI (clinical isolate) 15903); *Bacillus cereus* (ATCC 11778); *Pseudomonas aeruginosa* (ATCC 9027); and *Enterococcus faecalis* (ATCC 29212).

Minimal Inhibitory Concentration (MIC) Measurements:

Minimal inhibitory concentrations (MICs) were determined by microdilution susceptibility testing in 96-well plates using inocula of $10^6$ bacteria per ml.

Cell populations were evaluated by optical density measurements at 600 nm and were calibrated against a set of standards. Hundred (100) μl of a bacterial suspension were added to 100 μl of culture medium (control) or to 100 μl of culture medium containing various polymer concentrations in 2-fold serial dilutions. Inhibition of proliferation was determined by optical density measurements after an incubation period of 24 hours at 37° C.

Alternatively, MICs were determined using the microbroth dilution assay recommended by the Clinical and Laboratory Standards Institute (CLSI) using two-fold serial dilutions in cation-adjusted Mueller-Hinton broth (CAMHB).

Clinical bacterial isolates were obtained from Tel Aviv Sourasky Medical Center, Israel. Bactericidal kinetics was assessed using the drop plate method [see, for example, Chen et al., *Journal of Microbiological Methods*, November, 55(2): 475-9, 2003; and Skerman V. B. D., 1969, Abstracts of Microbiological Methods, p. 143-161, Wiley-Interscience, New York]. Statistical data for each experiment were obtained from at least two independent assays performed in duplicates.

Experimental Results

Preparation of Libraries of Polymers:

Several representative series of polymers according to the present invention, which are substantially comprised of a plurality of lysine residues and ω-amino-fatty acid residues and fatty acid residues as hydrophobic moieties, were prepared according to the general procedure described above, and are presented in Table 3 below.

These exemplary polymers are referred to in this section according to the following formula:

$$T[NC_iK(x)]_jG \text{ or Cyclic-}T[NC_iK(x)]_jG$$

In this formula, the prefix "Cyclic-" denotes a cyclic polymer; $NC_i$ denotes an ω-amino-fatty acid residue (an exemplary hydrophobic moiety according to the present invention, represented by $D_1 \ldots D_n$ in the general formulae I and II described herein), whereby i denotes the number of carbon atoms in the fatty acid residue; K denotes a lysine residue (an exemplary amino acid residue according to the present invention, denoted as $A_1 \ldots A_n$ in the general Formulae I and II described herein, such that [$NC_iK(x)$] denotes a residue of an ω-amino-fatty acid-lysine conjugate (denoted as [$A_1$-$Z_1$-$D_1$] [An-Zn-Dn] in the general Formulae I and II described herein) wherein (x) denotes the type of amine group in the amino acid used for conjugation with one end of the hydrophobic moiety (e.g., the ω-amino-fatty acid), whereby when the denotation (x) is absent, it is meant that conjugation is effected via the N-alpha of the lysine residue and when (x) is (ε) it is meant that conjugation is effected via the epsilon amine of the lysine residue; j denotes the number of the repeating units of a specific conjugate in the polymer (corresponding to n in the general Formulae I and II described herein); and T and G each independently denotes either a hydrogen (no denotation), a lysine residue (denoted K), an ω-amino-fatty acid residue (denoted $NC_i$), a fatty acid residue (denoted $C_i$), an ω-amino-fatty acid-lysine conjugate residue (denoted $NC_iK$), a fluorenylmethyloxycarbonyl residue (denoted Fmoc), a benzyl residue (denoted Bz), a cholate residue (denoted Chl), an amine group (typically forming an amide at the C-terminus and denoted $NH_2$), and free acid residue (for the C-terminus no denotation), an alcohol residue, and any combination thereof (all corresponding to X and Y in the general formula I described herein).

Thus, for example, a polymer according to the present invention which is referred to herein as $C_{12}K(\epsilon)NC_{12}K(\epsilon)NH_2$, corresponds to a polymer having the general formula I described hereinabove, wherein: X is a residue of a conjugate of a fatty acid having 12 carbon atoms (lauric acid) and lysine; n is 1 hence not denoted; $A_1 \ldots A_2$ are each a lysine residue, both conjugated via the epsilon amine hence denoted $K(\epsilon)$; $D_1$ is a residue of an ω-amino-fatty acid having 12 carbon atoms (12-amino-lauric acid); $Z_1 \ldots Z_2$ and $W_1$ are all peptide bonds; and Y is an amine. For clarity, the chemical structure of $C_{12}K(\epsilon)NC_{12}K(\epsilon)NH_2$ is presented in Scheme 2 below:

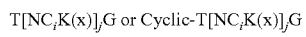

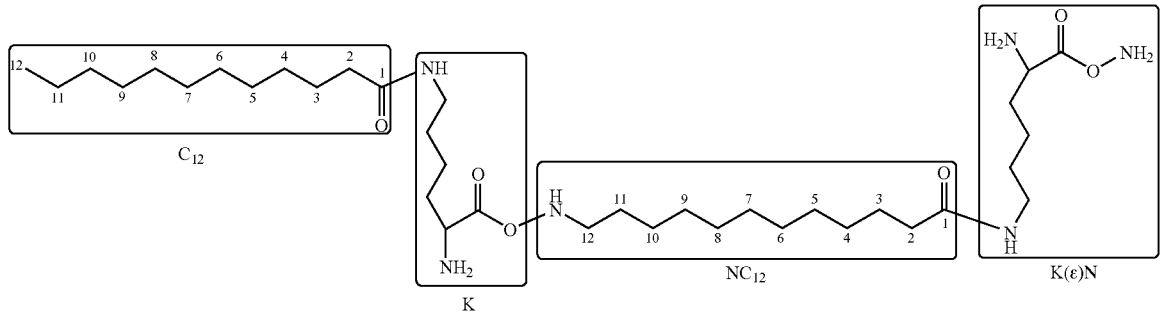

Minimal Inhibitory Concentration Measurements:

The polymers in each series were tested for various antimicrobial activities, as described hereinabove. The obtained results are presented in Table 3 below, wherein:

"Q" represents the overall molecular charge at physiological pH (column 3 in Table 3);

"ACN (%)" represents the percent of acetonitrile in the HPLC-RP gradient mobile phase at which the polymer was eluted and which corresponds to the estimated hydrophobicity of the polymer (column 4 in Table 3);

"MIC E.c." represents the minimal inhibitory concentration of each tested polymer in μM for *E. coli*, measured as described hereinabove in the antibacterial activity assay (column 5 in Table 3);

"MIC EDTA E.c." represents the minimal inhibitory concentration of each tested polymer in μM for *E. coli* culture in the presence of 2 mM EDTA, measured as described hereinabove for the enhanced outer-membrane permeability assay (column 6 in Table 3);

"MIC P.a." represents the minimal inhibitory concentration of each tested polymer in μM for *P. aeruginosa*, measured as described hereinabove for the antibacterial activity assay (column 7 in Table 3);

"MIC MR S.a." represents the minimal inhibitory concentration of each tested polymer in μM for methicillin-resistant *S. aureus*, measured as described hereinabove for the antibacterial activity assay of antibiotic-resistant bacteria (column 8 in Table 3);

"MIC B.c." represents the minimal inhibitory concentration of each tested polymer in μM for *Bacillus cereus*, measured as described hereinabove for the antibacterial activity assay (column 9 in Table 3); and "MIC E.f." represents the minimal inhibitory concentration of each tested polymer in μM for *Enterococcus faecalis*, measured as described hereinabove for the antibacterial activity assay (column 10 in Table 3); and ND denotes "not determined".

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED BY NUMERALS

Other References are Cited within the Text

1. National Nosocomial Infections Surveillance (NNIS) report, data summary from October 1986-April 1996,

TABLE 3

| I No. | II Polymer | III Q | IV ACN (%) | V MIC E.c. | VI MIC EDTA E.c. | VII MIC P.a. | VIII MIC MR S.a. | IX MIC B.c | X MIC E.f. |
|---|---|---|---|---|---|---|---|---|---|
| 1 | Cyclic-K(NC$_{12}$K)$_3$ | 4 | 44.2 | 50 | ND | 25 | 6.25 | ND | 12.5 |
| 2 | Cyclic-K(NC$_{12}$K)$_5$ | 6 | 46.6 | 12.5 | ND | 12.5 | 6.25 | ND | 6.25 |
| 3 | Cyclic-(NC$_{12}$K)$_2$ | 2 | 49.7 | >50 | ND | >50 | >50 | ND | >50 |
| 4 | Cyclic-(NC$_{12}$K)$_3$ | 3 | 47.0 | >50 | ND | >50 | 12.5 | >50 | ND |
| 5 | Cyclic-(NC$_{12}$K)$_4$ | 4 | 47.4 | >50 | ND | >50 | >50 | >50 | ND |
| 6 | Cyclic-(NC$_{12}$K)$_5$ | 5 | 47.7 | 12.5 | ND | 50 | 12.5 | >50 | ND |
| 7 | Cyclic-(KNC$_{12}$K)$_2$ | 4 | 40.7 | >50 | ND | 25 | 50 | ND | 50 |
| 8 | Cyclic-(KNC$_{12}$K)$_3$ | 6 | 41.7 | 25 | ND | 12.5 | 25 | ND | 25 |
| 9 | Cyclic-NC$_{12}$KKNC$_{12}$K | 3 | 42.7 | >50 | ND | 50 | 50 | ND | 25 |
| 10 | Cyclic-NC$_{12}$K(KNC$_{12}$K)$_2$ | 5 | 43.1 | 12.5 | ND | 12.5 | 12.5 | ND | 6.25 |
| 11 | Cyclic-KNC$_{12}$KKKNC$_{12}$K | 5 | 38 | >50 | ND | 12.5 | >50 | ND | >50 |
| 12 | Cyclic-KNC$_{12}$KKKNC$_{12}$KK | 6 | 35 | >50 | ND | >50 | >50 | ND | >50 |
| 13 | C$_{12}$K(ε)NC$_{12}$K(ε)NH$_2$ | 2 | 54.4 | 12.5 | ND | >50 | 12.5 | ND | 12.5 |
| Ref. 1 | MSI-78 | 10 | 44 | 50 | ND | 3.1 | >50 | 37.5 | 37.5 |
| Ref. 2 | IB-367 | 5 | 45 | 3.1 | ND | 12.5 | 3.1 | ND | ND |
| Ref. 3 | K$_4$S$_4$(1-16) | 6 | 47 | 3.1 | ND | 6.3 | 6.3 | 3.1 | 3.1 |
| Ref. 4 | LL37 | 11 | 61 | 50 | ND | 12.5 | ND | 37.5 | 37.5 |
| Ref. 5 | Ciprofloxacin | ND | ND | 0.05 | ND | 0.3 | >50 | 0.3 | 0.3 |
| Ref. 6 | Imipenem | ND | ND | 0.6 | ND | 16.4 | >50 | <0.03 | <0.03 |
| Ref. 7 | Tetracycline | ND | ND | 1.8 | ND | >50 | 0.4 | 0.07 | 0.07 |
| Ref. 8 | Rifampin | ND | ND | 7.7 | ND | 15.2 | 0.006 | 0.09 | 0.09 |

MSI-78, IB-367, K$_4$S$_4$(1-16) and LL37 are exemplary antimicrobial peptides known in the art, and Ciprofloxacin, Imipenem, Tetracycline and Rifampin are exemplary classical antibiotics known in the art, all serving as a reference for antimicrobial activity measurements.

As can be seen in Table 3 presented hereinabove and in Table 3 presented in U.S. patent application Ser. Nos. 11/234,183 and 11/500,461 and WO 2006/035431, by the present assignee, which are all incorporated herein by reference as if fully set forth herein, the cyclic polymers exhibited in general higher antimicrobial activity as compared to their linear counterparts, particularly against the *P. aeruginosa*, and the methicillin-resistant *S. aureus* strains. Similarly the polymer wherein the lysine was attached to the hydrophobic moieties via the epsilon amine of its side-chain exhibited higher antimicrobial activity as compared to its counterpart polymer wherein the lysine was attached to the hydrophobic moieties via the alpha amine thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

issued May 1996. *A report from the National Nosocomial Infections Surveillance (NNIS) System*. Am J Infect Control, 1996. 24(5): p. 380-8.

2. National Nosocomial Infections Surveillance (NNIS) System report, data summary from January 1990-May 1999, issued June 1999. Am J Infect Control, 1999. 27(6): p. 520-32.

3. Acar, J. F., *Consequences of bacterial resistance to antibiotics in medical practice*. Clin Infect Dis, 1997. 24 Suppl 1: p. S17-8.

4. Cohen, M. L., *Epidemiology of drug resistance: implications for a post-antimicrobial era*. Science, 1992. 257(5073): p. 1050-5.

5. Cosgrove, S. E. and Y. Carmeli, *The impact of antimicrobial resistance on health and economic outcomes*. Clin Infect Dis, 2003. 36(11): p. 1433-7.

6. Holmberg, S. D., S. L. Solomon, and P. A. Blake, *Health and economic impacts of antimicrobial resistance*. Rev Infect Dis, 1987. 9(6): p. 1065-78.
7. Feder, R., A. Dagan, and A. Mor, *Structure-activity relationship study of antimicrobial dermaseptin S4 showing the consequences of peptide oligomerization on selective cytotoxicity*. J Biol Chem, 2000. 275(6): p. 4230-8.
8. Krugliak, M., et al., *Antimalarial activities of dermaseptin S4 derivatives*. Antimicrob Agents Chemother, 2000. 44(9): p. 2442-51.
9. Levy, O., *Antimicrobial proteins and peptides of blood: templates for novel antimicrobial agents*. Blood, 2000. 96(8): p. 2664-72.
10. Zasloff, M., *Antimicrobial peptides in health and disease*. N Engl J Med, 2002. 347(15): p. 1199-200.
11. Zasloff, M., *Antimicrobial peptides of multicellular organisms*. Nature, 2002. 415(6870): p. 389-95.
12. Zasloff, M., *Innate immunity, antimicrobial peptides, and protection of the oral cavity*. Lancet, 2002. 360(9340): p. 1116-7.
13. Tossi, A., L. Sandri, and A. Giangaspero, *Amphipathic, alpha-helical antimicrobial peptides*. Biopolymers, 2000. 55(1): p. 4-30.
14. Latham, P. W., *Therapeutic peptides revisited*. Nat Biotechnol, 1999. 17(8): p. 755-7.
15. Darveau, R. P., et al., *Beta-lactam antibiotics potentiate magainin 2 antimicrobial activity in vitro and in vivo*. Antimicrob Agents Chemother, 1991. 35(6): p. 1153-9.
16. Giacometti, A., et al., *In-vitro activity and killing effect of polycationic peptides on methicillin-resistant Staphylococcus aureus and interactions with clinically used antibiotics*. Diagn Microbiol Infect Dis, 2000. 38(2): p. 115-8.
17. Appendini, P. and J. H. Hotchkiss, *Antimicrobial activity of a 14-residue synthetic peptide against foodborne microorganisms*. J Food Prot, 2000. 63(7): p. 889-93.
18. Brul, S. and P. Coote, *Preservative agents in foods. Mode of action and microbial resistance mechanisms*. Int J Food Microbiol, 1999. 50(1-2): p. 1-17.
19. Johnsen, L., et al., *Engineering increased stability in the antimicrobial peptide pediocin PA-1*. Appl Environ Microbiol, 2000. 66(11): p. 4798-802.
20. Yaron, S., et al., *Activity of dermaseptin K4-S4 against foodborne pathogens*. Peptides, 2003. 24(11): p. 1815-21.
21. Knight, L. C., *Non-oncologic applications of radiolabeled peptides in nuclear medicine*. Q J Nucl Med, 2003. 47(4): p. 279-91.
22. Lupetti, A., et al., *Radiolabelled antimicrobial peptides for infection detection*. Lancet Infect Dis, 2003. 3(4): p. 223-9.
23. Welling, M. M., et al., *Technetium-99m labelled antimicrobial peptides discriminate between bacterial infections and sterile inflammations*. Eur J Nucl Med, 2000. 27(3): p. 292-301.
24. Haynie, S. L., G. A. Crum, and B. A. Doele, *Antimicrobial activities of amphiphilic peptides covalently bonded to a water-insoluble resin*. Antimicrob Agents Chemother, 1995. 39(2): p. 301-7.
25. Alan, A. R., A. Blowers, and E. D. Earle, *Expression of a magainin-type antimicrobial peptide gene (MSI-99) in tomato enhances resistance to bacterial speck disease*. Plant Cell Rep, 2004. 22(6): p. 388-96.
26. Samaranayake, L. P. and N. W. Johnson, *Guidelines for the use of antimicrobial agents to minimise development of resistance*. Int Dent J, 1999. 49(4): p. 189-95.
27. *House of Lords inquiry into antimicrobial resistance*. Commun Dis Rep CDR Wkly, 1998. 8(17): p. 147, 150.

What is claimed is:

1. A cyclic polymer comprising a plurality of positively charged amino acid residues, an ω-amino fatty acid residue, one residue that has a first functional group and one residue that has a second functional group, wherein said ω-amino fatty acid residue is covalently linked to an amine group of one amino acid residue and a carboxyl group of another amino acid residue in said plurality of positively charged amino acid residues, and wherein the first functional group and the second functional group are covalently linked therebetween to form a cyclizing moiety, thereby forming the cyclic polymer, wherein said ω-amino fatty acid is selected from the group consisting of 8-amino-caprylic acid, 10-amino-capric acid, 12-amino-lauric acid, 14-amino-myristic acid, 16-amino-palmitic acid, 18-amino-stearic acid, 18-amino-oleic acid, 16-amino-palmitoleic acid, 18-amino-linoleic acid, 18-amino-linolenic acid and 20-amino-arachidonic acid.

2. The cyclic polymer of claim 1, having the general Formula II:

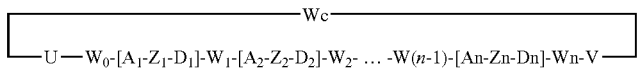

Formula II wherein:
n is an integer from 2 to 50;
$A_1, A_2, \ldots A_n$ are each independently a positively charged amino acid residue;
$D_1, D_2, \ldots D_n$ are each independently an ω-amino fatty acid residue or absent, provided that at least one of said $D_1, D_2, \ldots D_n$ is an ω-amino fatty acid residue;
$Z_1, Z_2, \ldots Z_n$ and $W_1, W_2, \ldots W_{n-1}$ are each independently a linking moiety linking two residues or absent;
$W_0$ is a linking moiety linking one of said $A_1, Z_1$ and $D_1$ to U, or absent;
$W_n$ is a linking moiety linking one of said $A_n, Z_n$ and $D_n$ to V, or absent;
U is selected from the group consisting of a first functional group, an amino acid residue having a first functional group, an ω-amino fatty acid residue having a first functional group, and a linking moiety having a first functional group or absent;
V is selected from the group consisting of a second functional group, an amino acid residue having a second functional group, an ω-amino fatty acid residue having a second functional group, and a linking moiety having a second functional group or absent; and
$W_c$ is said cyclizing moiety.

3. The polymer of claim 1, comprising two ω-amino fatty acid residues, wherein at least one of said two ω-amino fatty acid residues is linked to the N-alpha of an amino acid residue at the N-terminus of said plurality of positively charged amino acid residues and/or the C-alpha of an amino acid residue at the C-terminus of said plurality of positively charged amino acid residues.

4. The polymer of claim 1, wherein each of said positively charged amino acid residues is a lysine residue.

5. The polymer of claim 1, further comprising at least one active agent attached thereto.

6. The polymer of claim 5, being capable of delivering at least one active agent to a pathogenic microorganism.

7. The polymer of claim 1, having an antimicrobial activity.

8. The polymer of claim 7, being capable of selectively destructing a pathogenic microorganism.

9. A pharmaceutical composition comprising, as an active ingredient, the polymer of claim 1 and a pharmaceutically acceptable carrier.

10. The pharmaceutical composition of claim 9, being packaged in a packaging material and identified in print, in or on said packaging material, for use in the treatment of a medical condition associated with a pathogenic microorganism.

11. The pharmaceutical composition of claim 9, further comprising at least one additional therapeutically active agent.

12. A method of treating a medical condition associated with a pathogenic bacteria, the method comprising administering to a subject in need thereof a therapeutically effective amount of the polymer of claim 1.

13. The method of claim 12, further comprising administering to said subject at least one therapeutically active agent.

14. A medical device comprising the polymer of claim 1 and a delivery system configured for delivering said polymer to a bodily site of a subject.

15. A food preservative comprising an effective amount of the polymer of claim 1.

16. An imaging probe for detecting a pathogenic microorganism, the imaging probe comprising the polymer of claim 1, whereas said polymer further includes at least one labeling agent attached.

* * * * *